United States Patent [19]

Tsutsumi et al.

[11] Patent Number: 5,359,066
[45] Date of Patent: Oct. 25, 1994

[54] CERTAIN TRICYCLIC PYRIDO[3,2,1-IJ]CINNOLINE-8-CARBOXYLATES, USEFUL AS ANTIMICROBIAL AGENTS

[75] Inventors: Hideo Tsutsumi, Toyonaka; Takeshi Terasawa, Osaka; David Barrett, Nara; Masayoshi Murata, Osaka; Kazuo Sakane, Kawanishi; Akira Yazaki; Satoshi Inoue, both of Hiroshima, all of Japan

[73] Assignees: Wakunaga Pharmaceutical Co., Ltd.; Fujisawa Pharmaceutical Co., Ltd., both of Osaka, Japan

[21] Appl. No.: 938,249

[22] PCT Filed: Feb. 27, 1992

[86] PCT No.: PCT/JP92/00215

§ 371 Date: Jun. 15, 1993

§ 102(e) Date: Jun. 15, 1993

[87] PCT Pub. No.: WO92/15584

PCT Pub. Date: Sep. 17, 1992

[30] Foreign Application Priority Data

Feb. 28, 1991 [JP] Japan ................. 3-120674
May 31, 1991 [JP] Japan ................. 3-229848
Jul. 4, 1991 [JP] Japan ................. 3-164356
Aug. 27, 1991 [JP] Japan ................. 3-298555

[51] Int. Cl.$^5$ ............... C07D 471/06; C07D 487/06; A61K 31/50
[52] U.S. Cl. ..................... 544/234; 546/81
[58] Field of Search ................. 546/81; 544/234

[56] References Cited

U.S. PATENT DOCUMENTS 4,762,831 8/1988 Grohe et al. ............ 514/230.2
4,801,584 1/1989 Yokose et al. ........... 514/183
5,254,685 10/1993 Yokomoto et al. ........ 544/234

Primary Examiner—Alan L. Rotman
Attorney, Agent, or Firm—Oblon, Spivak, McClelland, Maier & Neustadt

[57] ABSTRACT

A compound represented by the following general formula:

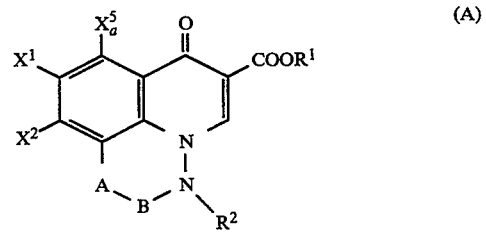

which is useful as an intermediate for production of a clinically excellent synthetic antibacterial, a salt thereof, and a process for producing the same.

In said formula,
$R^1$ is a hydrogen atom or a carboxyl-protecting group;
$R^2$ is a hydrogen atom or a lower alkyl group;
$X^1$ is a hydrogen atom or a halogen atom;
$X^2$ is a halogen atom;
$X_a^5$ is a hydrogen atom or a halogen atom;
A is a methylene group; a group of $>CH-COOR^4$, etc.,
in which $R^4$, $R^5$ and $R^6$ each are a hydrogen atom or a carboxyl-protecting group;
B is a methylene group or a carbonyl group;
provided that both A and B must not be methylene groups at the same time.

4 Claims, No Drawings

CERTAIN TRICYCLIC PYRIDO[3,2,1-IJ]CINNOLINE-8-CARBOXYLATES, USEFUL AS ANTIMICROBIAL AGENTS

TECHNICAL FIELD

The present invention relates to new tricyclic compounds. More concretely, it relates to new tricyclic compounds or sales thereof which are useful as intermediates for producing synthetic microbicides excellently suitable to clinical use, and also to a process for preparing them.

Accordingly, one object of the present invention is to provide new tricyclic compounds or salts thereof which are useful as intermediates for producing synthetic microbicides excellently suitable to clinical use.

Another object of the present invention is to provide a new industrial process for preparing such tricyclic compounds or salts thereof, which is excellent in point of the yield and purity of the products.

DISCLOSURE OF THE INVENTION

New tricyclic compounds of the present invention are compounds or salts thereof which are represented by the following general formula:

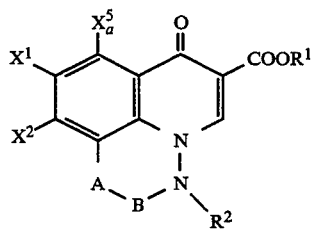

(A)

where

R$^1$ is a hydrogen atom or a carboxyl-protecting group;

R$^2$ is a hydrogen atom or a lower alkyl group;

X$^1$ is a hydrogen atom or a halogen atom;

X$^2$ is a halogen atom;

X$_a^5$ is a hydrogen atom or a halogen atom;

A is a methylene group; a group of >CH—COOR$^4$, or a group of:

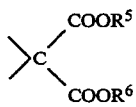

in which R$^4$, R$^5$ and R$^6$ each are a hydrogen atom or a carboxyl-protecting group;

B is a methylene group or a carbonyl group; provided that both A and B must not be methylene groups at the same time.

In accordance with the present invention, tricyclic compounds (A) can be prepared by the process (1) or process (2) as illustrated in the following schemes.

Process 1

Step 1-A

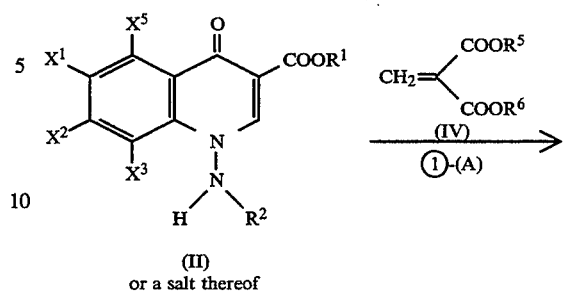

(II) or a salt thereof

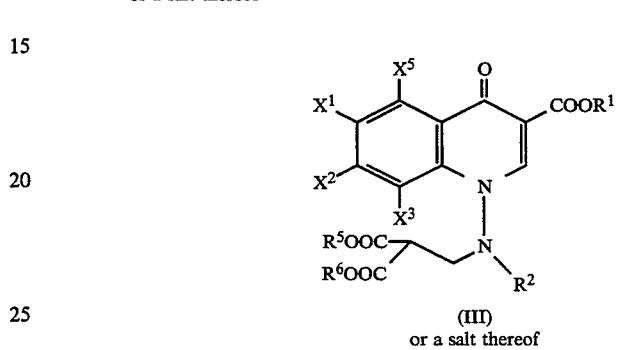

(III) or a salt thereof

Step 1-B

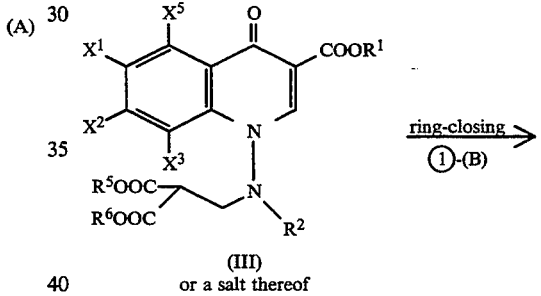

(III) or a salt thereof

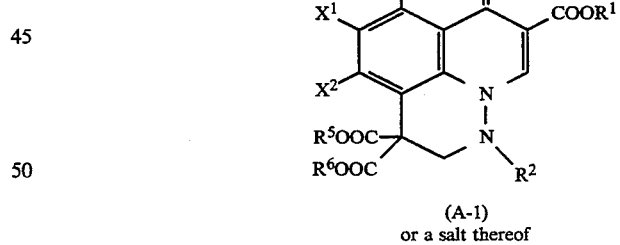

(A-1) or a salt thereof

Step 2

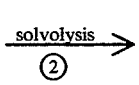

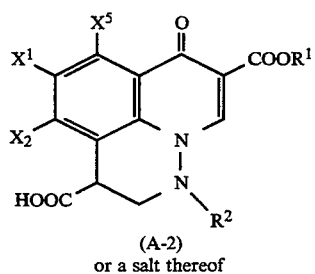

(A-2) or a salt thereof

Step 3

-continued

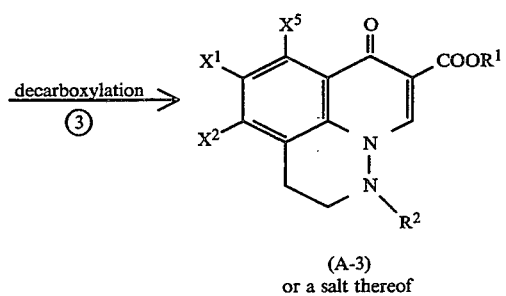

(A-3)
or a salt thereof

Step 4-A

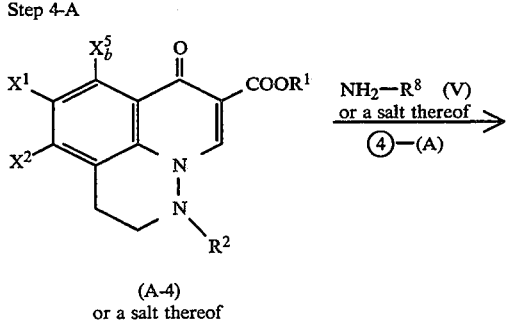

(A-4)
or a salt thereof

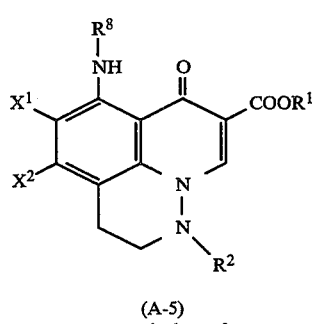

(A-5)
or a salt thereof

Step 4-B elimination of amino-protecting group
④-(B)

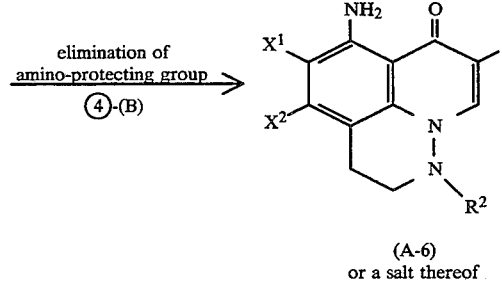

(A-6)
or a salt thereof

Step 5

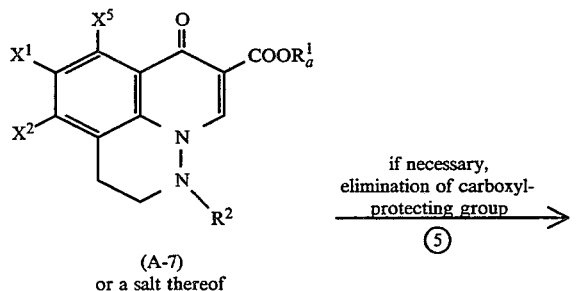

(A-7)
or a salt thereof if necessary, elimination of carboxyl-protecting group
⑤

-continued

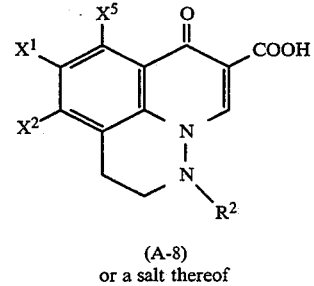

(A-8)
or a salt thereof

Process 2

Step 1

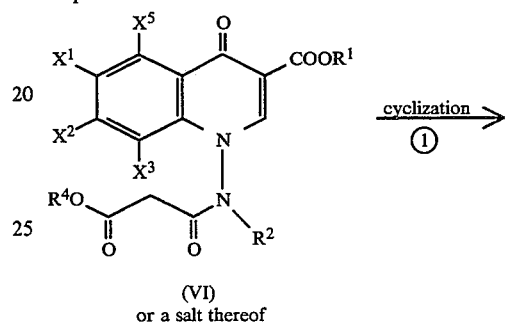

(VI)
or a salt thereof cyclization ①

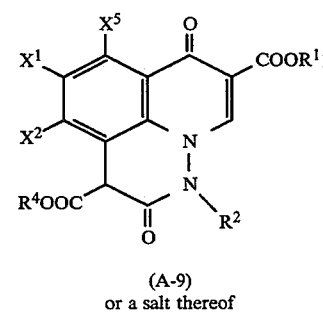

(A-9)
or a salt thereof

Step 2 elimination ②

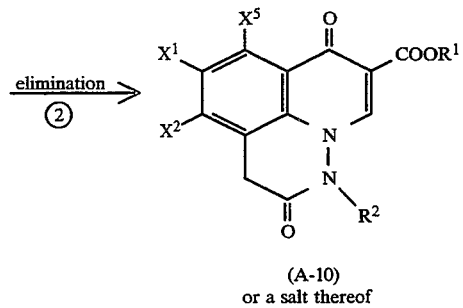

(A-10)
or a salt thereof

Step 3

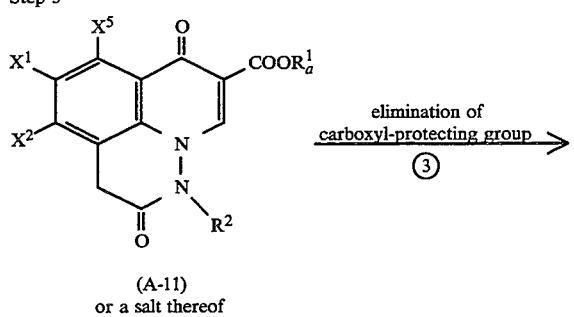

(A-11)
or a salt thereof elimination of carboxyl-protecting group
③

-continued

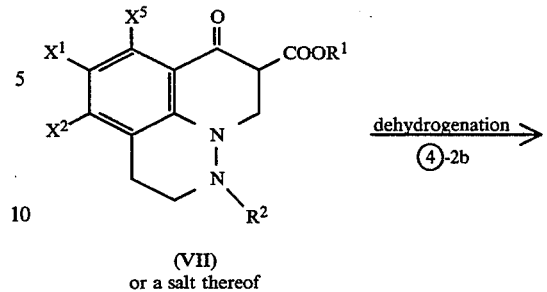

(VII)
or a salt thereof

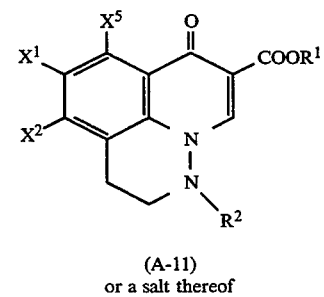

(A-11)
or a salt thereof or a salt thereof or a salt thereof
wherein
R¹, R², R⁴, R⁵, R⁶, X¹ and X² are each as defined above,
R⁸ is an amino-protecting group,
X³ is a split-off group,
X⁵ is a hydrogen atom, a halogen atom, an amino group or a protected amino group,
$X_b^5$ is a halogen atom, and
$R_a^1$ is a carboxyl- protecting group.

The starting compounds (II), (III) and (IV) can be prepared, for example, by the following processes each comprising a series of the illustrated steps.

Process A

Step a

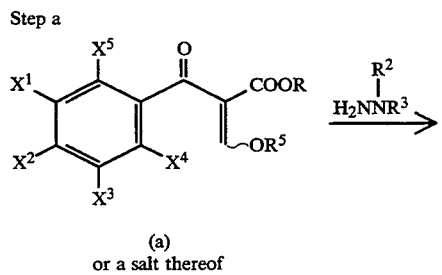

(a)
or a salt thereof

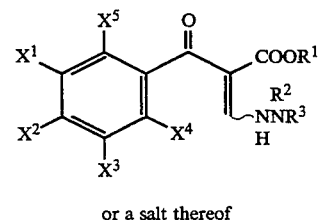

or a salt thereof

Step b

-continued

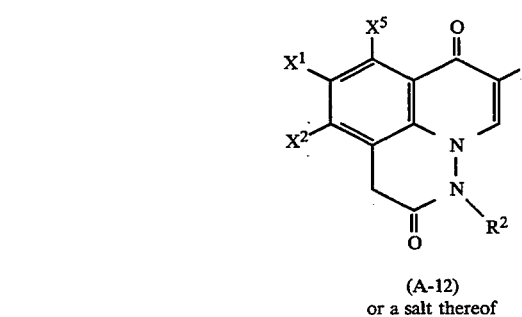

(A-12)
or a salt thereof

Step 4-1

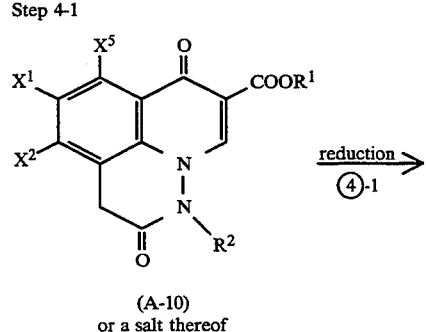

(A-10)
or a salt thereof

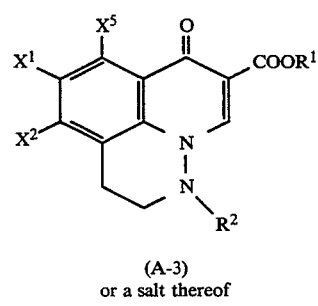

(A-3)
or a salt thereof

Step 4-2a

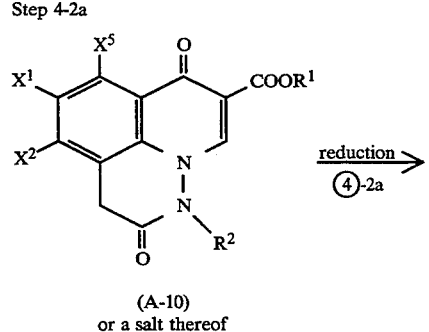

(A-10)
or a salt thereof

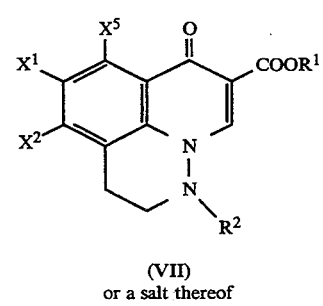

(VII)
or a salt thereof

Step 4-2b

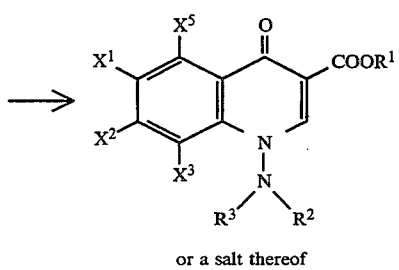
or a salt thereof
Step c
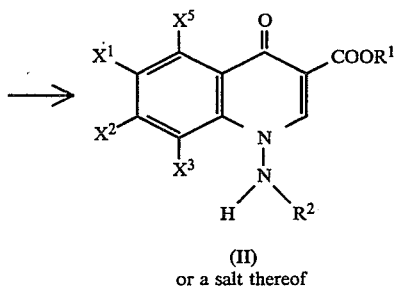
(II)
or a salt thereof
Step d
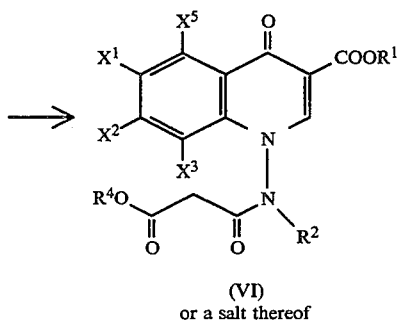
(VI)
or a salt thereof
Process B
Step a
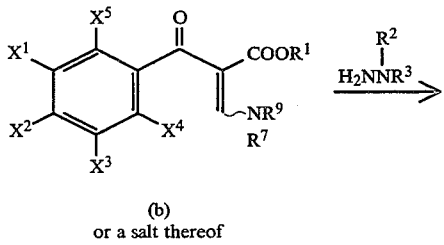
(b)
or a salt thereof
Step b
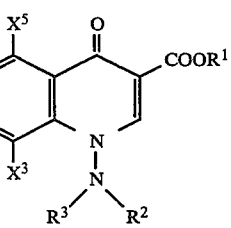
or a salt thereof
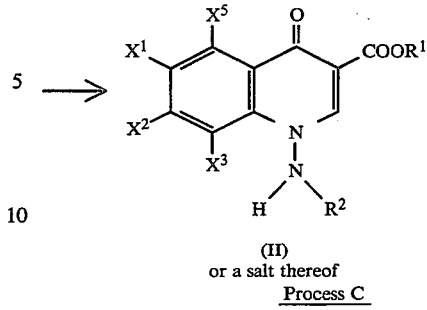
(II)
or a salt thereof
Process C
Step a
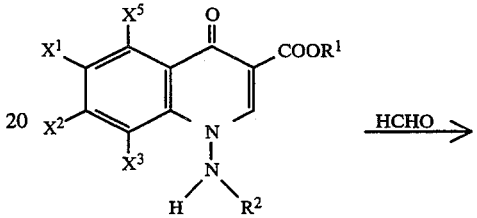
(II)
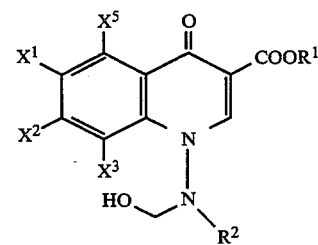
Step b
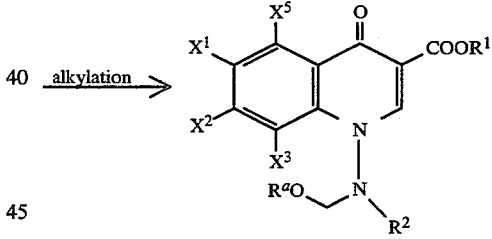
Step c
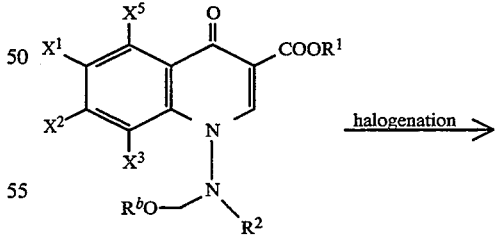
Step d
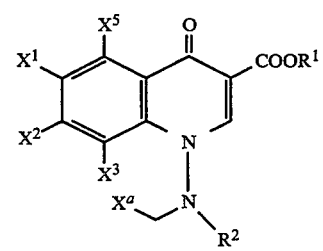

-continued

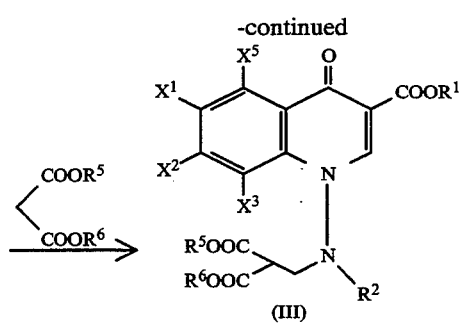

(III)

wherein $R^1$, $R^2$, $R^4$, $R^5$, $R^6$, $X^1$, $X^2$, $X^3$ and $X^5$ are each as defined above, $R^3$ is an amino-protecting group, $R^7$ and $R^9$ are each lower alkyl, $X^4$ is a split-off group, $R^a$ is a lower alkyl, $R^b$ is a hydrogen atom, or a lower alkyl, $X^a$ is a halogen atom.

Suitable salts of compounds (A) are both acid-addition salts thereof and base-addition salts thereof. Acid-addition salts of compounds (A) include, for example, (a) salts thereof with mineral acids such as hydrochloric acid, sulfuric acid, etc.; (b) salts thereof with organic carboxylic acids such as formic acid, citric acid, trichloroacetic acid, trifluoroacetic acid, etc.; and (c) salts thereof with sulfonic acids such as methanesulfonic acid, benzenesulfonic acid, p-toluenesulfonic acid, mesitylenesulfonic acid, naphthalenesulfonic acid, etc. Base-addition salts of compounds (A) include, for example, (a) salts thereof with alkali metals such as sodium, potassium, etc.; (b) salts thereof with alkaline earth metals such as calcium, magnesium, etc.; (c) ammonium salts thereof; and (d) salts thereof with nitrogen-containing organic bases such as trimethylamine, triethylamine, tributylamine, pyridine, N,N-dimethylaniline, N-methylpiperidine, N-methylmorpholine, diethylamine, cyclohexylamine, procaine, dibenzylamine, 1-ephenamine, N,N'-dibenzylethylenediamine, etc.

In the above and subsequent description of this specification, suitable examples of the various definitions are explained in detail as follows:

The term "lower" is intended to mean 1 to 6, preferably 1 to 4, carbon atom(s), when the substituent is a linear or branched group; and to mean 3 to 7 carbon atoms, when it is a cyclic group.

The term "carboxyl-protecting group" indicates the ester residue of a carboxylate and is intended to mean anyone which may relatively easily be cleaved to give the corresponding free carboxyl group. Specific examples of the group include, for example, groups which may split off by treatment under mild conditions, for example, by hydrolysis or catalytic reduction, such as a lower alkyl group (e.g., methyl, ethyl, n-propyl, tert-butyl, etc.), a lower alkenyl group (e.g., vinyl, allyl, etc.), an aralkyl group (e.g., benzyl, benzhydryl, etc.), an aryl group (e.g., phenyl, etc.), etc.; and groups which may easily split off, such as a lower alkanoyloxy-lower alkyl group (e.g., acetoxymethyl, pivaloyloxymethyl, etc.), a lower alkoxycarbonyloxy-lower alkyl group (e.g., methoxycarbonyloxymethyl, 1-ethoxycarbonyloxyethyl, etc.), a lower alkoxymethyl group (e.g., methoxymethyl, etc.), a lactonyl group (e.g., phthalidyl, etc.), a boron group substituted by substituent(s) selected from a halogen atom, a lower alkanoyloxy group, a halo-(lower) alkanoyloxy group and an aroyloxy group (e.g., benzoyloxy, toluoyloxy, naphthoyloxy), such as difluoroboron etc., as well as a di-lower alkylamino-lower alkyl group (e.g., 1-dimethylaminoethyl, etc.), and a (5-methyl-2-oxol-4-yl)methyl group.

The term "lower alkyl" includes, for example, methyl, ethyl, isopropyl, tert-butyl, tert-pentyl, and the like.

The "split-off group" includes, for example, halogen atoms such as fluorine atom etc., which will be mentioned hereunder.

The "halogen" may include, chloro, bromo, fluoro and iodo.

Suitable "protecting groups" of the "protected amino group" include, for example, an acyl group, such as a lower alkanoyl group (e.g., formyl, acetyl, propionyl, pivaloyl, hexanoyl, etc.), a mono- (or di-or tri-)halo(-lower)alkanoyl group (e.g., chloroacetyl, bromoacetyl, dichloroacetyl, trifluoroacetyl, etc.), a lower alkoxycarbonyl group (e.g., methoxycarbonyl, ethoxycarbonyl, propoxycarbonyl, tert-butoxycarbonyl, tert-pentyloxycarbonyl, hexyloxycarbonyl, etc.), a carbamoyl group, an aroyl group (e.g., benzoyl, toluoyl, naphthoyl, etc.), an ar(lower)alkanoyl group (e.g., phenylacetyl, phenylpropionyl, etc.), an aryloxycarbonyl group (e.g., phenoxycarbonyl, naphthyloxycarbonyl, etc.), an aryloxy(-lower)alkanoyl group (e.g., phenoxyacetyl, phenoxypropionyl, etc.), an arylglyoxyloyl group (e.g., phenylglyoxyloyl, naphthylglyoxyloyl, etc.), an optionally substituted ar (lower)alkoxycarbonyl group (e.g., benzoyloxycarbonyl, phenethyloxycarbonyl, p-nitrobenzyloxycarbonyl, etc.); a substituted or unsubstituted ar(lower)alkylidene group (e.g., benzylidene, hydroxybenzylidene, etc.); and an ar(lower)alkyl group, such as a mono-(or di- or tri-)phenyl(lower)alkyl group (e.g., benzyl, phenethyl, benzhydryl, trityl, etc.).

The "cyclo-lower alkylamino group" includes, for example, a cyclopropylamino group, a cyclobutylamino group, etc.

The "mono- or di-lower alkylamino group" includes, for example, a methylamino group, an ethylamino group, a dimethylamino group, a benzylamino group, etc.

The "cyclic amino group optionally having substituent(s)" may be either a saturated cyclic amino group or an unsaturated cyclic amino group and may contain additional one or more hetero atoms such as nitrogen, oxygen, sulfur atoms and others and/or carbonyl carbon atoms in the ring, and it may be mono-cyclic, bi-cyclic or tri-cyclic.

The cyclic amino group is preferably a saturated or unsaturated 4- to 9-membered ring, including, for example, an azetidinyl group, a pyrrolidinyl group, a piperidino group, a pyrrolinyl group, a pyrrolyl group, an imidazolyl group, a piperazinyl group, a homopiperazinyl group, a morpholino group, a thiomorpholino group, a 2,5-diazabicyclo[2.2.1]heptan-2-yl group, a 3,8-diazabicyclo[3.2.1]octan-8-yl group, a dihydroisoindolyl group, etc. Examples of substituents which may be into the cyclic amino group are a lower alkyl group, a lower alkenyl group, a lower aralkyl group, an aryl group, a hydroxyl group, a hydroxy-lower alkyl group, a substituted or unsubstituted amino group, a substituted or unsubstituted amino-lower alkyl group, a cyclic amino group as mentioned above, an alkoxy group, an alkoxy-lower alkyl group, a halogen atom, a halo-lower alkyl group, an acyloxy group, an acyloxy-lower alkyl group, an acyl group, a carboxyl group, a carboxy-lower alkyl group, an alkoxycarbonyl-lower alkyl group, a mercapto group, a lower alkylthio group, a cyano group, a nitro group, etc.

The alkyl group includes, for example, a methyl group, an ethyl group, an n-propyl group, etc.; the lower alkenyl group includes, for example, a vinyl group, an allyl group, etc.; a lower aralkyl group includes, for example, a benzyl group, a phenethyl group, etc.; the hydroxy-lower alkyl group includes, for example, a hydroxymethyl group, a hydroxyethyl group, a hydroxypropyl group, etc.; the amino-lower alkyl group includes, for example, an aminomethyl group, a 1-aminoethyl group, a 2-aminoethyl group, a 1-amino-1-methylethyl group, etc.; the alkoxy group includes, for example, a methoxy group, an ethoxy group, an n-propoxy group, etc.; the alkoxy-lower alkyl group includes, for example, a methoxymethyl group, an ethoxymethyl group, etc.; the halogen atom includes, for example, a fluorine atom, a chlorine atom, a bromine atom, etc.; the halo-lower alkyl group includes, for example, a fluoromethyl group, a trifluoromethyl group, etc.; the acyloxy group includes, for example, an acetoxy group, a benzoyloxy group, etc.; the acyloxy-lower alkyl group includes, for example, an acetoxymethyl group, a benzoyloxymethyl group, etc.; the acyl group includes, for example, those mentioned above, etc.; the carboxy-lower alkyl group includes, for example, a carboxymethyl group, a carboxyethyl group, etc.; the alkoxycarbonyl-lower alkyl group includes, for example, a methoxycarbonylmethyl group, a t-butoxycarbonylmethyl group, etc.; and the lower alkylthio group includes, for example, a methylthio group, an ethylthio group, etc.

Of those mentioned above, the substituents in the substituted amino group and the substituted amino-lower alkyl group include, for example, a lower alkyl group (e.g., methyl, ethyl, etc.), a lower cycloalkyl group (e.g., cyclopropyl, cyclobutyl, cyclopentyl, etc.), a lower alkenyl group (e.g., vinyl, allyl, etc.), a lower aralkyl group (e.g., benzyl, phenylethyl, etc.), an aryl group (e.g., phenyl, etc.), an acyl group (e.g., those mentioned above, etc.), an amino acid residue or peptide residue (e.g., Gly-, Leu-, Val-, Ala-, Phe-, Ala-Ala-, Gly-Val-, Gly-Gly-Val-, etc.), and a protected amino acid residue or peptide residue in which the functional group(s) is/are protected with protective group(s) which is/are ordinarily used in peptide chemistry, such as an acyl group, a lower aralkyl group, etc., and a cyclic amino group. The number of the substituents may be 1 to 3, and they may freely be selected from same or different ones. The amino acid-protecting group is preferably one which may split off from the compound and may be soluble in a body. Especially preferred is an alanyl group.

Where Y is a group of $R^{10}$—$(CH_2)m$—O— and $R^7$ is an optionally substituted amino group, nitrogen-containing saturated heterocyclic group or lower cycloalkyl group, the substituent(s) to be in the group of $R^7$ may be the same one(s) as that those to be in the above-mentioned cyclic amino group. The lower cycloalkyl group includes, for example, a cyclopropyl group, a cyclobutyl group, etc.; and the nitrogen-containing saturated heterocyclic group is preferably a 4- to 9-membered ring, which may be the same one as the saturated hetero ring as referred to for the above-mentioned cyclic amino group. Especially preferred is the hetero ring is a 3-azetidinyl group, a 3-pyrrolidinyl group, etc. The bond between the saturated heterocyclic group and —$(CH2)m$—O— may be at any atom in the ring of the former.

The processes for preparing the object compound (A) of the present invention are explained in detail in the following.

PROCESS 1

Step 1-A

The compound (III) or a salt thereof can be prepared by reacting a compound (II) or a salt thereof and a conjugated double bond-having compound (IV) by Michel addition reaction.

Suitable salts of the compounds (II) and (III) can be referred to the ones as exemplified for the compound (A).

The reaction is carried out in the presence of a base or a Lewis acid. Preferred base may include, for example, an alkali metal hydride such as sodium hydride, potassium hydride, etc.; an alkaline earth metal hydride such as calcium hydride, etc.; an alkali metal alkoxide such as potassium tert-butoxide, etc.; and potassium fluoride, etc. Preferred Lewis acid may include, for example, a zinc halide such as zinc bromide, zinc chloride, etc.; a magnesium halide such as magnesium bromide, magnesium chloride, etc.; a titanium compound such as titanium tetrachloride, tetraethoxy titanium, tetrapropoxy titanium, etc.; boron trifluoride, etc.

The reaction is usually carried out in a solvent such as water, an alcohol [e.g., methanol, ethanol, etc.], methylene chloride, tetrahydrofuran, N,N-dimethylformamide, dimethylsulfoxide, N-methylpyrrolidone, a mixture thereof or any other solvent which does not adversely influence the reaction.

As an auxiliary agent which may be used along with the solvent or Lewis acid, for example, mentioned are compounds having ether bond(s) for modifying the acidity of the Lewis acid, such as diethyl ether, 1,2-epoxypropane, tetrahydrofuran, dioxane, etc.

The reaction temperature is nor critical and the reaction is usually carried out under heating.

Step 1-B

The compound (A-1) or a salt thereof can be prepared by subjecting the compound (III) or a salt thereof to the ring-closing reaction.

Suitable salts of the compounds (A-1) can be referred to the ones as exemplified for the compound (A).

The ring-closing reaction is effected in the presence of a base. As suitable examples of the base and solvent, those illustrated in the step 1-A are referred to.

The reaction temperature is not critical and the reaction is usually carried out under heating.

Depending upon the reaction condition (for example, using dimethylsulfoxide as the solvent), the ring-closing reaction of the step 1-B is effected simultaneously with the Michel addition of the step 1-A and the reaction progresses in one step as a whole.

Step 2

The compound (A-2) or a salt thereof can be prepared by subjecting the compound (A-1) or a salt thereof to the solvolysis reaction.

Suitable salts of the compounds (A-2) can be referred to the ones as exemplified for the compound (A).

Preferred base is an inorganic base or organic base, including, for example, an alkali metal such as sodium, potassium etc.; an alkaline earth metal such as magnesium, calcium, etc.; a hydroxide, carbonate or hydrogencarbonate of the metal; a trialkylamine such as trimethylamine, triethylamine, etc.; as well as picoline, 1,5-diazabicyclo[4.3.0]non-5-ene, 1,4-diazabicyclo[2.2.2]octane, 1,8-diazabicyclo[5.4.0]undec-7-ene, etc.

Preferred acid may include, for example, an organic acid such as formic acid, acetic acid, glacial acetic acid, propionic acid, trichloroacetic acid, trifluoroacetic acid, etc.; and an inorganic acid such as hydrochloric acid, hydrobromic acid, sulfuric acid, hydrogen chloride, hydrogen bromide, etc.

Removal to be effected by the use of a Lewis acid such as a trihaloacetic acid, for example, trichloroacetic acid, trifluoroacetic acid, etc., is preferably effected in the presence of a cation-capturing agent such as anisol, phenol, etc.

The reaction is usually carried out in a solvent such as water, an alcohol [e.g. methanol, ethanol, etc.], methylene chloride, tetrahydrofuran, N,N-dimethylformamide, dimethylsulfoxide, a mixture thereof or any other solvent which does not adversely influence the reaction. A liquid base or acid can be also used as the solvent.

The reaction temperature is not critical and the reaction is usually carried out under cooling to heating.

Step 3

The compound (A-3) or a salt thereof can be prepared by subjecting the compound (A-2) or a salt thereof to the decarboxylation reaction.

Suitable salts of the compounds (A-3) can be referred to the ones as exemplified for the compound (A).

The reaction is carried out under heating in an inert gas atmosphere such as nitrogen, etc. or by an ordinary method such as reduction.

The reaction is usually carried out in a solvent such as water, an alcohol [e.g.: methanol, ethanol, etc.], methylene chloride, tetrahydrofuran, N,N-dimethylformamide, dimethylsulfoxide, a mixture thereof or any other solvent which does not adversely influence the reaction.

The reaction temperature is not critical and the reaction is usually carried out under warming to heating.

Step 4-A

The compound (A-5) or a salt thereof can be prepared by reacting the compound (A-4) or a salt thereof with the amine compound(V) or a salt thereof.

Suitable salts of the compounds (A-4) and (A-5) can be referred to the ones as exemplified for the compound (A).

The reaction is generally effected by using an equivalent amount or a somewhat excess amount of the compound (V) or a salt thereof to the compound (A-2) or a salt thereof, in the presence of sodium carbonate, calcium carbonate, sodium hydrogencarbonate, triethylamine, DBU, etc. As the case may be, an excess amount of the compound (V) may be used, which has an additional role of an acid acceptor in the reaction.

The reaction may be effected, in general, in any solvent which does not have any bad influence on the reaction and which includes, for example, aromatic hydrocarbons such as benzene, toluene, xylene, etc.; ethers such as tetrahydrofuran, dioxane, monoglyme, etc.; halogenated hydrocarbons such as methylene chloride, chloroform, etc.; aprotonic polar solvents such as dimethylformamide, dimethylsulfoxide, etc.; and acetonitrile, pyridine, etc.

The reaction temperature is not critical and the reaction is usually carried out under warming to heating.

Step 4-B

The compound (A-6) or a salt thereof can be prepared by subjecting the compound (A-5) or a salt thereof to the elimination reaction of the amino-protecting group.

Suitable salts of the compounds (A-6) can be referred to the ones as exemplified for the compound (A).

To the reaction of removing the amino-protecting group, any ordinary reaction condition for hydrolysis or catalytic reduction may be applied. Concretely, in the case of hydrolysis, the reaction is effected in a solvent, for example, water; an alcohol such as methanol, ethanol, isopropyl alcohol, etc.; a ketone such as acetone, methyl ethyl ketone, etc.; an ether such as dioxane, ethylene glycol, diethyl ether, etc.; acetic acid, etc., or in a mixed solvent of them, in the presence of a basic compound such as sodium hydroxide, potassium hydroxide, barium hydroxide, potassium carbonate, etc.; a mineral acid such as sulfuric acid, hydrochloric acid, nitric acid, etc.; or an organic acid such as acetic acid or an aromatic sulfonic acid. The reaction is effected generally at room temperature to about 200° C., preferably room temperature to about 120° C.

In the case of catalytic reduction, the reaction is effected in a solvent such as methanol, ethanol, propanol, acetic acid, tetrahydrofuran, dioxane, ethyl acetate, water, etc., or in a mixed solvent of them, in the presence of a catalyst of palladium-carbon, palladium-black, platinum dioxide, etc., generally with stirring in a hydrogen stream of atomic pressure to 100 barometric pressures. The reaction temperature is at room temperature to about 100° C., and the reaction is finished generally in 1 to 48 hours.

Step 5

The compound (A-8) or a salt can be prepared by subjecting the compound (A-7) or a salt to the elimination reaction of the carboxyl-protecting group.

Suitable salts of the compounds (A-7) and (A-8) can be referred to the ones as exemplified for the compound (A).

To the reaction of removing the carboxyl-protecting group, any ordinary reaction condition for hydrolysis or catalytic reduction may be applied. Concretely, those mentioned in the previous step 4-B are referred to.

PROCESS (2)

Step 1

The compound (A-9) or a salt thereof can be prepared by subjecting the compound (VI) or a salt thereof to the cyclization reaction.

Suitable salts of the compounds (A-9) can be referred to the ones as exemplified for the compound (A).

The cyclization reaction is effected by an ordinary method such as dehydrohalogenation.

The reaction is preferably effected in the presence of a base. Preferred base may include, for example, an alkali metal hydride such as sodium hydride, potassium hydride, etc.; an alkaline earth metal hydride such as calcium hydride, etc.; an alkali metal alkoxide such as potassium tert-butoxide, etc.; potassium fluoride, etc.

The reaction is preferably effected in the presence of a copper salt, such as cuprous iodide, cuprous or cupric chloride, etc.

The reaction is usually carried out in a solvent such as water, an alcohol [e.g. methanol, ethanol, etc.], methylene chloride, tetrahydrofuran, N,N-dimethylformamide, dimethylsulfoxide, a mixture thereof or any other solvent which does not adversely influence the reaction.

The reaction temperature is not critical and the reaction is usually carried out under heating.

Step 2

The compound (A-10) or a salt thereof can be prepared by subjecting the compound (A-9) or a salt thereof to the elimination reaction.

Suitable salts of the compounds (A-10) can be referred to the ones as exemplified for the compound (A).

In the reaction of removing the esterified carboxyl group, both the deesterification and the decarboxylation are conducted simultaneously or successively.

The reaction is effected by an ordinary method such as solvolysis, reduction, etc.

The solvolysis is preferably effected in the presence of a base or an acid (including Lewis acids). Preferred base is an inorganic base or an organic base, including, for example, an alkali metal such as sodium, potassium, etc.; an alkaline earth metal such as magnesium, calcium, etc.; a hydroxide, carbonate or hydrogencarbonate of the metal; a trialkylamine such as trimethylamine, triethylamine, etc.; as well as picoline, 1,5-diazabicyclo[4.3.0]non-5-ene, 1,4-diazabicyclo[2.2.2]octane, 1,8-diazabicyclo[5.4.0]undec-7-ene, etc.

Preferred acid may include, for example, an organic acid such as formic acid, acetic acid, glacial acetic acid, propionic acid, trichloroacetic acid, trifluoroacetic acid, etc.; and an inorganic acid such as hydrochloric acid, hydrobromic acid, sulfuric acid, hydrogen chloride, hydrogen bromide, etc.

Removal to be effected by the use of a Lewis acid such as a trihaloacetic acid, for example, trichloroacetic acid, trifluoroacetic acid, etc., is preferably effected in the presence of a cation-capturing agent such as anisol, phenol, etc.

Reduction to be applied to the reaction includes chemical reduction and catalytic reduction. Regarding the reducing agents to be used for reduction, any and every conventional ones may be used. For instance, the chemical reducing agent may include, for example, combination of a metal such as tin, lead, iron, etc.; or a metal compound such as chromium chloride, chromium acetate, etc.; and an organic or inorganic acid such as formic acid, acetic acid, propionic acid, trifluoroacetic acid, p-toluenesulfonic acid, hydrochloric acid, hydrobromic acid, etc.; aluminium lithium hydride; sodium boron hydride; combination of sodium boron hydride and trifluoroacetic acid or pyridine; combination of sodium boron hydride and phosphoryl chloride; and borane-methylsulfide complex; and the catalyst for catalytic reduction may include, for example, a platinum catalyst such as platinum sheet, platinum sponge, platinum black, colloidal platinum, platinum oxide, platinum wire, etc.; a palladium catalyst such as palladium sponge, palladium black, palladium oxide, palladium-carbon, colloidal palladium, palladium-barium sulfate, palladium-barium carbonate, etc.; a nickel catalyst such as reduced nickel, oxidized nickel, Raney nickel, etc.; a cobalt catalyst such as reduced cobalt, Raney cobalt, etc.; an iron catalyst such as reduced iron, Raney iron, etc.; and a copper catalyst such as reduced copper, Raney copper, Ullmann copper, etc.

Where the group of $R^4$ is an allyl group, the reaction may be effected in the presence of an allyl group-capturing agent of capturing the allyl group to be generated in the reaction system, the allyl group-capturing agent including, for example, a palladium compound such as palladium acetate, tetrakis(triphenylphosphine) palladium(O), bis (dibenzylideneacetone) palladium(O), di[1,2-bis(diphenylphosphino)ethane] palladium(O), tetrakis(triphenyl phosphite) palladium (0), etc.; an amine such as morpholine, N-methylaniline; an active methylene compound such as dimedone, benzoyl acetate, 2-methoxy-3-oxo-valeric acid, etc.; a cyanohydrin compound such as cyanated α-tetrahydropyranyloxybenzyl, etc.; a lower alkanoic acid or a salt thereof such as formic acid, acetic acid, ammonium formate, sodium acetate, etc.; and N-hydroxysuccinimide, etc. The reaction is more preferably effected in the presence of triphenylphosphine, etc.

The reaction is usually carried out in a solvent such as water, an alcohol [e.g. methanol, ethanol, etc.], methylene chloride, tetrahydrofuran, dioxane, N,N-dimethylformamide, ethylene glycol dimethyl ether, a mixture thereof or any other solvent which does not adversely influence the reaction. A liquid base or acid can be also used as the solvent.

The reaction temperature is not critical and the reaction is usually carried out under cooling to heating.

Step 3

The compound (A-12) or a salt thereof can be prepared by subjecting the compound (A-11) or a salt thereof to the elimination reaction of the carboxyl-protecting group. Suitable salts of the compounds (A-11) and (A-12) can be referred to the ones as exemplified for the compound (A).

To the reaction of removing the carboxyl-protecting group, any ordinary reaction condition for hydrolysis or catalytic reduction may be applied. Concretely, those mentioned in the step 4-B in the process 1 are referred to.

Step 4-1

The compound (A-3) or a salt thereof can be prepared by reducing the compound (A-10) or a salt thereof.

As the reduction to be applied to the reaction, the ordinary reduction method as mentioned in the previous step 2 may be referred to.

Therefore, the above-mentioned explanation may be referred to.

Step 4-2a

The compound (VII) or a salt thereof can be prepared by reducing the compound (A-10) or a salt thereof.

Suitable salts of the compounds (VII) can be referred to the ones as exemplified for the compound (A).

The reaction is effected, for example, in the presence of a reducing agent, such as sodium boron hydride, combination of sodium boron hydride and boron trifluoride-diethyl ether complex, etc.

The reaction is usually carried out in a solvent such as pyridine, tetrahydrofuran or any other solvent which does not adversely influence the reaction.

The reaction temperature is not critical and the reaction is usually carried out under cooling to heating.

Step 4-2b

The compound (A-11) or a salt thereof can be prepared by subjecting the compound (VII) or a salt thereof to the dehydrogenation reaction.

The reaction is effected, for example, in the presence of a catalyst such as manganese dioxide, etc.

The reaction is usually carried out in a conventional solvent which does not adversely influence the reaction such as ethyl acetate.

The reaction temperature is not critical and the reaction is usually carried out under cooling to heating.

The compounds obtained by the above Process 1(step 1 to step 5) to Process 2 (step 1 to step 4) can be isolated and purified by a conventional method such as extraction, pulverization, precipitation, fractional crystallization, recrystallization, column chromatography, or the like.

Not only the compounds (A) are useful as a microbicide by themselves but also some of them are useful as intermediates for producing other microbicides of the same kind, which is described in Japanese Patent Application No. 2-211190.

For the reagents and the reaction conditions, for example, the solvents and the reaction temperatures, for the production methods A, B and C for the starting materials (II), (III) and (VI), for example, the preparation examples mentioned below are referred to. For the starting substances (a) and (b) in the production methods A and B, for example, the description of Japanese Patent Application Laid-Open No. 59-212474 and the preparation examples mentioned below are referred to.

The tricyclic compounds (A) or salts thereof may be converted to synthetic microbicides (B) which are advantageous to clinical use, in accordance with the preparation process mentioned below, which is similar to the process described in Japanese Patent Application No. 2-211190 or 3-80144.

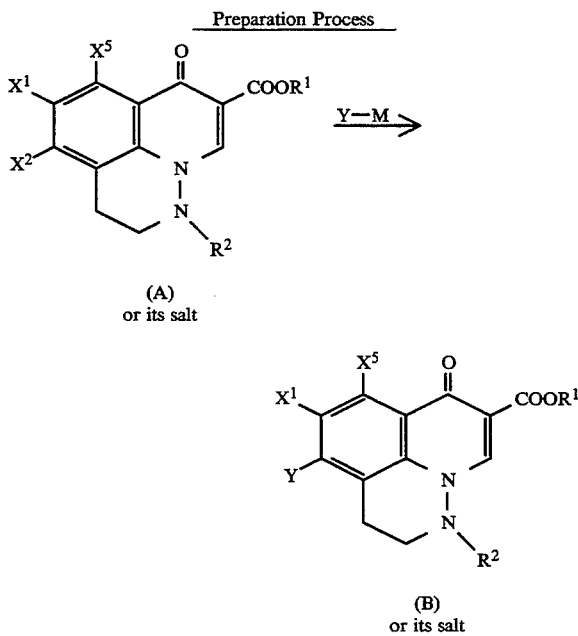

Preparation Process (A) or its salt (B) or its salt wherein $R^1$, $R^3$, $X^1$, $X^2$ and $X^5$ are each as defined above;

Y is an amino group, a cyclo-lower alkylamino group, a mono- or di-(lower)alkylamino group, an optionally substituted cyclic amino group, or a group of $R^{10}$—$(CH_2)_m$—O—, in which $R^{10}$ is a hydrogen atom, an optionally substituted amino group, an optionally substituted nitrogen-containing saturated heterocyclic group, or an optionally substituted lower cycloalkyl group, and m is an integer of 0 to 3; and M is a hydrogen atom or an alkali metal atom.

The compound (B) is obtained by reacting the compound (A) and an amine compound or a salt thereof or an alkali metal alcoholate of Y—M.

The salt of an amine to be used may be an acid-addition salt thereof.

The reaction is effected desirably in an inert reaction solvent such as acetonitrile, N,N-dimethylformamide, dimethylsulfoxide, sulforane or N-methylpyrrolidone or in a mixed solvent of them.

The reaction temperature is preferably 50° to 200° C., more preferably 80° to 150° C.

The reaction is desirably effected, with neutralizing the hydrogen halide to be generated during the reaction by the use of a base such as triethylamine, lutidine, 1,8-diazabicyclo[5.4.0]undeca-7-ene, 1,5-diazabicyclo[4.3.0]nona-5-ene, an alkali metal carbonate, etc. Neutralization of the hydrogen halide to be generated may also be effected by the use of an excess amount of the reactant alkali metal alcoholate or amine.

In the reaction, the product may often be obtained in the form of a salt thereof. If desired, the salt may be treated with an acid such as acetic acid, trifluoroacetic acid, hydrochloric acid, etc., or a base such as sodium carbonate, potassium carbonate, sodium hydroxide, potassium hydroxide, etc., so that the product is converted into the corresponding free form.

Next, the present invention will be explained by way of the following preparations and examples.

EXAMPLES

Preparation 1

A mixture comprising ethyl 2,3,4,5,6-pentafluorobenzoylacetate (28.6 g), ethyl orthoformate (23.2 g) and acetic anhydride (32.3 g) was heated under reflux for 8 hours. The mixture was concentrated under reduced pressure, then dissolved in methylene chloride (100 ml). To the solution was added methylene chloride (30 ml) solution of N-(tert-butoxycarbonyl)-N-methylhydrazine (14.6 g) at 0° ~ 10° C., stirred for 2 hours, and the solvent was removed by distillation. The oily product obtained was crystallized with n-hexane and filtered to obtain ethyl 2-(2,3,4,5,6-pentafluorobenzoyl)-3-(2-tert-butoxycarbonyl-2-methylhydrazino)acrylate (18.2 g).

To N,N-dimethylformamide (50 ml) solution of ethyl acrylate was added potassium carbonate (6.2 g) and heated at 70° C. for one hour. The mixture was poured into ice-cold water (200 ml), to give a solid. The solid was collected by filtration and dissolved in chloroform (200 ml), washed with water and dried over magnesium sulfate, and concentrated under reduced pressure. The oily product obtained was crystallized with n-hexane to obtain ethyl 1-(N-tert-butoxycarbonyl-N-methylamino)-5,6,7,8-tetrafluoro-1,4-dihydro-4-oxoquinoline-3-carboxylate (13.7 g).

Preparation 2

Ethyl 1-(N-tert-butoxycarbonyl-N-methylamino)-5,6,7,8-tetrafluoro -1,4-dihydro-4-oxoquinoline-3-carboxylate (4.2 g) was dissolved in ethyl acetate (30 ml),.

4N hydrochloric acid-dioxane solution (40 ml) was added thereto with ice-cooling and stirred overnight at room temperature, and the solvent was removed by distillation. The residue was dissolved in chloroform (100 ml), and 10% sodium carbonate aqueous solution (50 ml) was added thereto and stirred for 30 minutes at room temperature. The organic layer was separated out and dried over magnesium sulfate, and the solvent was removed by distillation. The crystals were dispersed in ether and filtered out to obtain ethyl 1-methylamino-5,6,7,8-tetrafluoro -1,4-dihydro-4-oxoquinoline-3-carboxylate (2.9 g).

Preparation 3

A solution of 1-tert-butoxycarbonyl-1-methylhydrazine(2.88 g) in ethanol (3 ml) was dropwise added to a solution of ethyl 2-(2,3,4,5-tetrafluorobenzoyl)-3-ethoxyacrylate(6.00 g) in ethanol (15 ml) at 0°∼10° C.

The mixture was stirred at 0°∼10° C. for 30 minutes and at ambient temperature for one hour. Diisopropyl ether (40 ml) was added to the mixture to give a solid. The solid was collected by filtration and dried over phosphorus pentaoxide under reduced pressure to give ethyl 2-(2,3,4,5-tetrafluorobenzoyl)-3-(2-tert-butoxycarbonyl-2-methylhydrazino)acrylate (6.41 g).

mp: 123°–124° C. IR(Nujol): 3175, 1720, 1678 cm$^{-1}$ NMR(CDCl$_3$, δ):isomerA 1.00(3H, t, J=7.1 Hz), 1.49(9H, s), 3.25(3H, s), 4.05 (2H, q, J=7.1 Hz), 8.02(1H, d, J=11.6 Hz), 10.29(1H, d, J=11.6 Hz) isomer B 1.14(3H, t, J=7.1 Hz), 1.50(9H, s), 3.29(3H, s), 4.11(2H, q, J=7.1 Hz), 8.08(1H, d, J=11.2 Hz), 11.75(1H, d, J=11.2 Hz)

Preparation 4

A suspension of ethyl 2-(2,3,4,5-tetrafluorobenzoyl)-3-(2-tert-butoxycarbonyl-2-methylhydrazino)acrylate (10.50 g)and potassium carbonate (3.80 g)in dimethylformamide (31.5 ml)was heated at 60°∼65° C. for one hour. The mixture was poured into ice-water (300 ml) to give a solid. The solid was filtered, dissolved in dichloromethane (100 ml), dried over magnesium sulfate, and concentrated under reduced pressure to give a residue. The residue was triturated with n-hexane to give ethyl 1-(N-tert-butoxycarbonyl-N-methylamino)-6,7,8-trifluoro-1,4-dihydro-4-oxoquinoline-3-carboxylate (9.25 g).

mp: 125°–126° C. IR(Nujol): 1732, 1720, 1695 cm$^{-1}$ NMR(CDCl$_3$, δ): 1.3–1.7(12H), 3.43(3H, s), 4.39(2H, d, J=7.1 Hz),8.12(1H, ddd, J=2.1 Hz, 7.8 Hz, 10.0 Hz), 8.37(1H, s)

Preparation 5

To 4N hydrochloric acid solution (46 ml) in ethyl acetate was added ethyl 1-(N-tert-butoxycarbonyl-N-methylamino)-6,7,8-trifluoro-1,4-dihydro-4-oxoquinoline-3-carboxylate (9.20 g) under ice-cooling and the mixture was stirred at the same condition for 2 hours. Diisopropyl ether (90 ml) was added to the mixture to give a solid. The solid was collected by filtration, and dried over phosphorus pentaoxide under reduced pressure to give ethyl 6,7,8-trifluoro-1-methylamino-1,4-dihydro -4-oxoquinoline-3-carboxylate hydrochloride(6.26 g).

mp: 137°–141° C. IR(Nujol): 1665 cm$^{-1}$ NMR(CDCl$_3$, δ): 1.41(3H, t, J=7.1 Hz), 2.98(3H, z), 4.38(2H, q, J=7.1 Hz), 8.15 (1H, ddd, J=2.2 Hz), 8.0 Hz, 10.1 Hz), 8.66(1H, s)

Preparation 6

To a solution of ethyl 6,7,8-trifluoro-1-methylamino-1,4-dihydro -4-oxoquinoline-3-carboxylate hydrochloride(5.91 g)in dichloromethane (100 ml) was added a saturated aqueous sodium hydrogencarbonate solution (50 ml) and the mixture was stirred at ambient temperature for 30 minutes. The organic layer was washed with brine (50 ml), dried over magnesium sulfate, and concentrated under reduced pressure to give a solid. The solid was recrystallized from dichloromethane-n-hexane to give ethyl 6,7,8-trifluoro-1-methylamino-1,4-dihydro-4-oxoquinoline-3-carboxylate (5.14 g).

mp: 149°–150° C. IR(Nujol): 1723 cm$^{-1}$ NMR(CDCl$_3$, δ): 1.39(3H, t, J=7.1 Hz), 2.98(3H, s), 4.36(2H, q, J=7.1 Hz), 8.12 (1H, ddd, J=2.2 Hz, 8.1 Hz, 10.1 Hz), 8.56(1H, s)

Preparation 7

A mixture of ethyl 2-(2,3,4,5-tetrafluorobenzoyl)-3-(2-tert-butoxycarbonyl-2-methylhydrazino)acrylate (2.00 g) and potassium fluoride (0.31 g) in dimethylformamide(5 ml) was heated at 60°∼65° C. for one hour, and refluxed for 5 hours. The mixture was poured into ice-water (60 ml) to give a solid. The solid was collected by filtration and dried over phosphorus pentaoxide under reduced pressure to give ethyl 6,7,8-trifluoro-1-methylamino-1,4-dihydro-4-oxoquinoline-3-carboxylate (1.25 g).

Preparation 8

To a mixture of ethyl 6,7,8-trifluoro-1-methylamino-1,4-dihydro-4-oxoquinoline-3-carboxylate (0.53 g) and allyl hydrogenmalonate (0.35 g) in dichloromethane (10 ml) was added 1-(3-dimethylaminopropyl)-3-ethylcarbodiimide hydrochloride (0.47 g) and the mixture was stirred at ambient temperature for 18 hours. The mixture was poured into a mixture of water (50 ml) and dichloromethane (50 ml). The organic layer was washed with water and ,next, brine, dried over magnesium sulfate, concentrated under reduced pressure, and triturated with methanol to give ethyl 1-{N-(allyloxycarbonyl)acetyl-N-methylamino}-6,7,8-trifluoro-1,4-dihydro-4-oxoquinoline-3-carboxylate (0.32 g).

Preparation 9

To a mixture of ethyl 6,7,8-trifluoro-1-methylamino-1,4-dihydro -4-oxoquinoline-3-carboxylate (600 g) and 1,3-bis(trimethylsilyl)urea (2.25 g) was stirred at ambient temperature for 15 minutes. To this mixture was added allyl malonyl chloride (3.57 g) and the solution was stirred at ambient temperature for one hour. The mixture was washed with water (60 ml), saturated aqueous sodium hydrogencarbonate solution (60 ml), and brine (60 ml) in turn, dried over magnesium sulfate, and concentrated under reduced pressure to give a syrup. The syrup was crystallized from a mixture of acetone and diisopropyl ether to give ethyl 1-{N-(allyloxycarbonyl)acetyl-N-methylamino}-6,7,8-trifluoro-1,4-dihydro-4-oxoquinoline-3-carboxylate (8.01 g).

mp: 124°–126° C. IR(Nujol): 1740, 1730, 1707, 1683 cm$^{-1}$ NMR(CDCl$_3$, δ): isomer A 3.36(3H, s), 8.29(1H, s) isomer B 3.48(3H, s), 8.43(1H, s) MS: 426(M$^+$), 381(M$^+$), 369, 353, 338

Preparation 10

To a solution of ethyl 6,7,8-trifluoro-1-methylamino-1,4-dihydro -4-oxoquinoline-3-carboxylate (3.00 g)and diphenylmethyl hydrogenmalonate (2.70 g) in dichloromethane (60 ml) was added 1-(3-dimethylaminopropyl)-3-ethylcarbodiimide hydrochloride(2.30 g) under ice-cooling. The mixture was stirred at the same condition for 30 minutes and at ambient temperature for one hour. The mixture was poured into water (60 ml). The organic layer was washed with water (60 ml)and next brine (60 ml), dried over magnesium sulfate, and concentrated under reduced pressure to give a syrup. The syrup was subjected to a column chromatography on silicagel (50 g) and eluted with chloroform and a mixture of methanol and chloroform (1:99 v/v) to give ethyl 1-{N-(diphenylmethyloxycarbonyl) acetyl-N-methylamino}-6,7,8-trifluoro-1,4-dihydro-4-oxoquinoline-3-carboxylate (3.73 g) as a glass.

IR(CHCl$_3$): 1740, 1697 cm$^{-1}$ MS: 552(M+), 342, 323, 296

Preparation 11

To a solution of ethyl 6,7,8-trifluoro-1-methylamino-1,4-dihydro -4-oxoquinoline-3-carboxylate (1.00 g)in dichloromethane (10 ml) was added 1,3-bis (trimethylsilyl)urea(0.37 g) and the mixture was stirred at ambient temperature for 30 minutes. To the mixture was added ethyl malonyl chloride (0.46 ml) and the solution was stirred at ambient temperature for 2 hours. Dichloromethane was added to the solution. The solution was washed with water (20 ml), saturated aqueous sodium hydrogencarbonate (20 ml), and brine (20 ml), in turn, dried over magnesium sulfate, and concentrated under reduced pressure to give a residue. The residue was crystallized from a mixture of acetone and diisopropyl ether to give ethyl 1-{N-(ethoxycarbonyl)acetyl-N-methylamino}-6,7,8-trifluoro -1,4-dihydro-4-oxoquinoline-3-carboxylate (1.14 g).

Preparation 12

To a solution of ethyl 6,7,8-trifluoro-1-methylamino-1,4-dihydro 4-oxoquinoline-3-carboxylate (0.50 g) in pyridine (3 ml) was added ethyl malonyl chloride (0.23 ml)) under ice-cooling and the mixture was stirred at the same temperature for 2 hours. The mixture was poured into ice-water (50 ml) to give a solid. The solid was collected by filtration and dried over phosphorus pentaoxide under reduced pressure to give ethyl 1-{N-(ethoxycarbonyl)acetyl-N-methylamino}-6,7,8-trifluoro-1,4-dihydro-4-oxoquinoline-3-carboxylate (0.84 g).

mp: 149°–151° C. IR(Nujol): 1740–1730, 1707, 1685 cm$^{-1}$ NMR(CDCl$_3$, δ): isomerA 3.82(3H, s), 8.29(1H, s) isomerB 3.48(3H, s), 8.43(1H, s) MS: 414(M+), 369, 342, 300, 270

Preparation 13

To dioxane (80 ml) solution of 2,3,4,5-tetrafluorobenzoyl chloride (21.25 g) was added dioxane (25 ml) solution of methyl 3-dimethylaminoacrylate (12.92 g) with ice-cooling, and triethylamine (14.46 ml) was added thereto with ice-cooling. The mixture was stirred for 30 minutes at the same temperature, then for 3 hours at room temperature, and then for one hour at 50° to 60° C. The mixture was concentrated under reduced pressure, then dissolved in methylene chloride (200 ml), washed with water (200 ml) and brine (100 ml) in order, then dried with sodium sulfate and concentrated under reduced pressure to obtain a syrup product. The syrup product was subjected to column chromatography with silica gel and eluted with a mixed liquid of methanol/methylene chloride (3/97, V/V) to obtain methyl 3-dimethylamino-2-(2,3,4,5-tetrafluorobenzoyl)acrylate (15.47 g) as a syrup product.

IR(CHCl$_3$): 1700–1685, 1625 cm$^{-1}$ NMR(CDCl$_3$, δ): 2.89(3H, brs), 3.35(3H, brs), 3.85(3H, s), 7.17–7.31(1H, m), 7.83(1H, s) MS: 305, 273

Preparation 14

To methylene chloride (120 ml) solution of methyl 3-dimethylamino -2-(2,3,4,5-tetrafluorobenzoyl)acrylate (13.2 g) was added methylene chloride (12 ml) solution of 1-tert-butoxycarbonyl-1-methylhydrazine (7.59 g) with ice-cooling, and the mixture was stirred for one hour at the same temperature and then for 15 hours at room temperature. The reaction mixture was concentrated under reduced pressure. The residue was triturated with diisopropyl ether (132 ml). The solid formed was taken out by filtration and dried with phosphorus pentaoxide under reduced pressure to obtain methyl 1-(N-tert-butoxycarbonyl-N-methylamino)-6,7,8-trifluoro-1,4-dihydro-4-oxoquinoline-3-carboxylate (10.49 g).

mp: 141°–145° C. IR(Nujol): 3400, 1732, 1698 cm$^{-1}$ NMR(CDCl$_3$, δ): 1.33(3H, s), 1.56(6H, s), 3.43(3H, s), 3.96(3H, s), 8.13(ddd, J=2.2 Hz, 8.1 Hz, 10.0 Hz), 8.41(1H, s) Ms: 386(M+), 371, 330, 286, 272, 254

Preparation 15

To ethyl acetate solution (55 ml) of 4N hydrochloric acid, was added methyl 1-(N-tert-butoxycarbonyl-N-methylamino)-6,7,8-trifluoro-1,4-dihydro-4-oxoquinoline-3-carboxylate (10.85 g) with ice-cooling, and the mixture was stirred for one hour at the same temperature and then for 14 hours at room temperature. The mixture was concentrated under reduced pressure to obtain a solid. The solid was poured into a mixture comprising methylene chloride (150 ml) and water (150 ml). The suspension was neutralized with sodium hydrogencarbonate. The precipitates were taken out by filtration, washed with water and dried with phosphorus pentaoxide to obtain a solid. The solid was recrystallized from a liquid mixture of methylene chloride and diisopropyl ether to obtain methyl 6,7,8-trifluoro-1-methylamino-1,4-dihydro-4-oxoquinoline-3-carboxylate (4.05 g).

mp: 190°–191° C. IR(Nujol): 3260, 1730 cm$^{-1}$ NMR(DMSO-d$_6$, δ): 2.84(3H, d, J=5.7 Hz), 3.77(3H, s), 6.97(1H, q, J=5.7 Hz), 7.97(1H, ddd, J=2.2 Hz, 8.31 Hz, 10.5 Hz), 8.65(1H, s) MS: 286, 255, 228, 211

Preparation 16

A suspension of ethyl 1-methylamino-6,7,8-trifluoro-1,4-dihydro-4-oxoquinoline-3-carboxylate (10 g) in water (100 ml) and 37% aqueous formaldehyde (100 ml) was heated to 100° C. for 1 hour. The mixture was cooled and the solid removed by filtration and washed with water. The resulting yellow colored solid was dried to constant weight in vacuo over phosphorus pentaoxide to yield ethyl 1-[N-(hydroxymethyl)-N-methylamino]-6,7,8-trifluoro-1,4-dihydro-4-oxoquinoline-3-carboxylate (10.25 g).

IR( Nujol ): 3425, 1710, 1620 cm$^{-1}$ NMR(DMSO-d$_6$, δ): 1.28(3H, t, J=7 Hz), 3.00(3H, s), 4.25(2H, q, J=7Hz), 4.66–4.50(2H, m), 6.30(1H, t, J=6.5 Hz), 7.98–7.87(1H, m), 8.95(1H, s)

Preparation 17

A solution of ethyl 1-[N-(hydroxymethyl)-N-methylamino]-6,7,8-trifluoro-1,4-dihydro-4-oxoquinoline-3-carboxylate (8.4 g) and triethylamine (3.09 g) in methylene chloride (150 ml) was cooled to 0° C. and treated with acetyl chloride (2.18 g). After 3 hours the reaction was diluted with water and shaken in a separating funnel. The organic layer was dried over magnesium sulfate, evaporated, and the crude product purified by chromatography with silica gel (50% ethyl acetate-hexane elution) to yield ethyl 1-[N-(ethoxymethyl)-N-methylamino]-6,7,8-trifluoro-1,4-dihydro-4-oxoquinoline-3-carboxylate (2.1 g).

IR(Nujol): 1720, 1610, 1560 cm$^{-1}$ NMR (CDCl$_3$-ppm, δ): 1.26(3H, t, J=7 Hz), 1.41(3H, t, J=7.1 Hz), 3.12(3H, s), 3.67–3.43(2H, m), 4.47–4.32(2H, m), 4.54(2H, s), 8.15–8.05(1H, m), 9.05(1H, s) Mass (EI): 358(M+) Elemental Analysis for C$_{16}$H$_{17}$F$_3$ N$_2$ O$_4$ Calcul.: C 53.63 H 4.78 N 7.82 Found: C 53.88 H 4.78 N 7.62

Preparation 18

To a solution of ethyl 1-(ethoxymethyl)methylamino-6,7,8-trifluoro-1,4-dihydro-4-oxoquinoline-3-carboxylate (200 mg) in dry acetonitrile (2.0 ml) was added trichloromethylsilane (65.8 μl) under ice-cooling and the mixture was stirred for 30 minutes, and then for 10 minutes at room temperature. To the reaction mixture was added diisopropyl ether (10 ml), which was then stirred for 15 minutes at ambient temperature. The precipitate was collected by filtration and washed with diisopropyl ether and dried in vacuo over phosphorus pentaoxide to give ethyl 1-(chloromethyl)methylamino-6,7,8-trifluoro-1,4-dihydro-4-oxoquinoline-3-carboxylate (145 mg).

IR(Nujol): 1720, 1600, 1480, 1340 cm$^{-1}$ Elemental Analysis for C$_{14}$H$_{12}$ClF$_3$ N$_2$ O$_3$ Calcul.: C 48.22 H 3.47 N 8.03 Cl 10.17 Found: C 48.45 H 3.53 N 8.01 Cl 9.77

Preparation 19

To a solution of ethyl 1-[N-(hydroxymethyl)m-N-ethylamino]-6,7,8-trifluoro-1,4-dihydro-4-oxoquinoline-3-carboxylate (3.0 g) in dry-dichloromethane(60 ml) was added trichloromethylsilane (1.18 ml) under ice-cooling and the mixture was stirred for 1.5 hours at the same temperature. To the reaction mixture was added diisopropyl ether (120 ml), which was then stirred for 2 hours at ambient temperature. The precipitate was collected by filtration and washed with diisopropyl ether and n-hexane and dried in vacuo over phosphorus pentaoxide to give ethyl 1-[N-(chloromethyl)-N-methylamino]-6,7,8-trifluoro-1,4-dihydro-4-oxoquinoline-3-carboxylate (3.07 g).

IR(Nujol): 1720, 1600, 1480, 1340 cm$^{-1}$ NMR (CDCl$_3$, δ): 1.41(3H, t, J=7 Hz), 3.20(3H, s), 4.40(2H, q, J=7 Hz), 5.39–5.52(2H, m), 8.02–8.12(1H, m), 9.01(1H, s)

Preparation 20

To dimethylformamide (1.5 ml) solution of diethyl malonate (47.8 μl), was added sodium hydride (24.4 mg) with stirring under ice-cooling, and the mixture was stirred for 20 minutes with ice-cooling. To the solution was added ethyl 1-[N-(chloromethyl)-N-methylamino]-6,7,8-trifluoro-1,4-dihydro-4-oxoquinoline-3-carboxylate (100 mg) with stirring under ice-cooling, and the mixture was stirred for 30 minutes at the same temperature. The reaction solution was added to a mixed solution comprising ethyl acetate (30 ml) and water (30 ml) for extraction. The organic layer was washed with water (30 ml×3) and a saturated brine(30 ml×3), dried over magnesium sulfate and concentrated under reduced pressure. The residue thus obtained was subjected to column chromatography with silica gel (3 g), eluted with a mixed solvent of dichloromethane ethyl acetate (20/1 to 10/1) and concentrated to dryness under reduced pressure to obtain ethyl 6,7,8-trifluoro-1-[N-methyl-N-{2,2-bis(ethoxycarbonyl)ethyl}amino]-1,4-dihydro-4-oxoquinoline-3-carboxylate (49.1 mg).

IR (Nujol): 1715, 1610, 1560, 1480, 1350 cm−1 NMR (CDCl3, δ): 1.16–1.29(6H, m), 1.42(3H, t, J=7 Hz), 3.03(3H, s), 3,47(1H, t, J=7 Hz), 3.60–3.74(2H, m), 4.05–4.30 (4H, m), 4.41(2H, q, J=7 Hz), 8.04–8.14(1H, m), 8.62(1H, s)

Preparation 21

In a similar manner as in Preparation 20, the following compound was obtained.
Ethyl 6,7,8-trifluoro-1-[N-methyl-N-{2,2-bis(tert-butoxycarbonyl) ethyl}amino]-1,4-dihydro-4-oxoquinoline-3-carboxylate IR(Nujol): 1715, 1610, 1560, 1480, 1350, 1220 cm$^{-1}$ NMR (CDCl$_3$, δ): 1.38(9H, s), 1.42(3H, t, J=7 Hz), 1.45(9H, s), 3.01(3H, s), 3.25(1H, t, J=7 Hz), 3.51–3.65(2H, m), 4.42(2H, q, J=7 Hz), 8.05–8.15(1H, m) 8.63(1H, s)

Example 1

To dimethylsulfoxide (2.0 ml) solution of ethyl 6,7,8-trifluoro-1-methylamino-1,4-dihydro-4-oxoquinoline-3-carboxylate (105 mg) and tert-butyl 2-tert-butoxycarbonylacrylate (87.8 mg), was added solid potassium tert-butoxide (43.2 mg), and the mixture was stirred for 6 hours and then for 30 minutes at room temperature. Next, this was heated at 90° C., for 2 hours, then cooled and allowed to stand at room temperature overnight. This was diluted with ethyl acetate, washed once with 1N hydrochloric acid and four times each with water, dried over magnesium sulfate and concentrated under reduced pressure to obtain an orange syrup product (134.8 mg). The syrup product was subjected to column chromatography with silica gel and eluted with a mixed solvent of methylene chloride, ethyl acetate (10/1) to obtain ethyl 4,5-difluoro-2,3-dihydro-1-methyl-7-oxo-1H, 7H-pyrido[3,2,1-i,j]cinnoline-3,3-bis(tert-butoxycarbonyl)-8-carboxylate (36.6 mg) as a pale yellow syrup product.

NMR(CDCl3, δ): 1.37(3H, t, J=7 Hz), 1.48(18H, s), 2.78(3H, s), 4.08(2H, s,) 4.39(2H, q, J=7 Hz), 8.29(1H, dd, J=8 and 10 Hz), 8.55(1H, s) MS(EI)M/Z: 508(M+), 452(MH+—But), 408(MH+—CO2But), 509(MH+)

Example 2

Trifluoroacetic acid (1.0 ml) was added to methylene chloride (1.0 ml) solution of ethyl 4,5-difluoro-2,3-dihydro-1-methyl-7-oxo-1H, 7H-pyrido[3,2,1-i, j]-cinnoline-3,3-bis(tert-butoxycarbonyl)-8-carboxylate (36.5 mg), with ice-cooling, and this was stirred for 15 minutes at 5° C. or lower and then allowed to stand at room temperature for 24 hours. The solvent of the reaction mixture was removed by distillation, and aqueous sodium hydrogencarbonate solution was added to the residue, which was then extracted with methylene chloride (2×5 ml). The basic layer was acidified with 1M hydrochloric acid, which was then extracted with methylene chloride (4×5 ml). These extracts were combined and dried over magnesium sulfate. Then, the solvent was removed therefrom under reduced pressure, and the residue was dried to solid to obtain ethyl 4,5-difluoro-2,3-dihydro-1-methyl-7-oxo-1H, 7H-pyrido[3,2,1-i, j]cinnoline-3-carboxy-8-carboxylate (7.40 mg) as a white solid. The aqueous layer was extracted twice each with ethyl acetate and dried over magnesium sulfate, and the solvent was removed by distillation to obtain ethyl 4,5-difluoro-2,3-dihydro-1-methyl-7-oxo-1H, 7H-pyrido[3,2,1-i, j]cinnoline-3 -carboxy-8-carboxylate (6.10 mg).

NMR(DMSO-d6, δ): 1.28(3H, t, J=7.1 Hz), 2.82(3H, s), 3.84–3.70(2H, m), 4.22(2H, q, J=7.1 Hz), 4.30(1H, t, J=5.6 Hz), 8.07(1H, dd, J=8.6 and 10.6 Hz), 8.53(1H, s)

Example 3

Dimethylsulfoxide (0.5 ml) solution of ethyl 4,5-difluoro-2,3-dihydro-1-methyl-7-oxo-1H, 7H-pyrido[3,2,1-i, j]cinnoline-3-carboxy-8-carboxylate(7.4 mg) was heated at 170° C., in an nitrogen atmosphere for 30 minutes, then cooled, diluted with ethyl acetate, washed with water (4 times), dried over magnesium sulfate and filtered, and the solvent was removed by distillation under reduced pressure to obtain ethyl 4,5-difluoro-2,3-dihydro-1-methyl-7-oxo-1H, 7H-pyrido[3,2,1-i, j]cinnoline-8-carboxylate (7.4 mg) as a white solid.

NMR(CDCl3, δ): 141(3H, t, J=7 Hz), 2.87(3H, s), 3.06(2H, t, J=6 Hz), 3.50(2H, t, J=6 Hz), 4.39(2H, q, J=7 Hz), 8.15(1H, dd, J=8.6 and 8.6 Hz), 8.58(1H, s)

Example 4

Solid potassium tert-butoxide (823 mg) was added to tetrahydrofuran (40 ml) solution of ethyl 6,7,8-trifluoro-1-methylamino-1,4-dihydro-4-oxoquinoline-3-carboxylate (2.0 g) and tert-butyl 2-tert-butoxycarbonylacrylate (1.67 g), with stirring and suspending under ice-cooling, and the suspension was stirred for 0.5 hour with ice-cooling and then 1.5 hours at room temperature. The reaction solution was poured into a mixed liquid of ethyl acetate ice-water (150 ml/150 ml) and was adjusted to have pH of 3.0 with 1N hydrochloric acid. The organic layer was separated out, washed with water and saline solution, and dried over magnesium sulfate. This was concentrated under reduced pressure to obtain an amorphous product. The amorphous product was subjected to column chromatography with silica gel and eluted with a mixed solvent of methylene chloride ethyl acetate (20/1 to 10/1). The fractions containing the object product were collected, and the solvent was removed by distillation under reduced pressure. The residue was tritulated with n-hexane, and the precipitates were filtered out to obtain ethyl 6,7,8-trifluoro-1-[N-methyl-N-{2,2-bis(tert-butoxycarbonyl)ethyl}amino]-1,4 -dihydro-4-oxoquinoline-3-carboxylate (1.35 g) as an almost white powder.

The filtrate was evaporated and dried to solid to also obtain the same compound ethyl 6,7,8-trifluoro-1-[N-methyl-N-{2,2-bis(tert-butoxycarbonyl)ethyl}amino]-1,4-dihydro-4-oxoquinoline-3-carboxylate (330 mg).

NMR(CDCl3, δ): 1.38(9H, s), 1.45(9H, s), 1.49(3H, t, J=7 Hz), 3.01(3H, s), 3.25 (1H, t, J=7 Hz), 3.51–3.70(2H, m), 4.41(2H, q, J=7 Hz), 8.05–8.15(1H, m), 8.64(1H, s)

Example 5

Methylene chloride (10 ml) solution of ethyl 6,7,8-trifluoro-1-methylamino-1,4-dihydro-4-oxoquinoline-3-carboxylate (1.0 g) and tert-butyl 2-tert-butoxycarbonylacrylate (1.52 g) was cooled in an ice bath in nitrogen atmosphere, and titanium tetrachloride (632.4 mg) was dropwise added thereto. After 30 minutes, this was diluted with ethyl acetate (100 ml) and then with water (100 ml). The organic layer was separated out, washed with water (2×50 ml), dried over magnesium sulfate and concentrated under reduced pressure to obtain an yellow syrup product. The syrup product was subjected to column chromatography with silica gel and eluted with a mixed solvent of methylene chloride/ethyl acetate (10/1) to obtain ethyl 6,7,8-trifluoro-1-[N-methyl-N-{2,2-bis(tert-butoxycarbonyl)ethyl}amino]-1,4-dihydro-4-oxoquinoline-3-carboxylate (988 mg), as a white solid.

Example 6

N-methylpyridone (10 ml) solution of ethyl 6,7,8-trifluoro-1-[N-methyl-N-{2,2-bis(tert-butoxycarbonyl)ethyl}amino]-1,4-dihydro-4-oxoquinoline-3-carboxylate (500 mg) was stirred at room temperature, and potassium tert-butoxide (117 mg) was added thereto. The solution was stirred for 15 minutes at room temperature and then for 3.5 hours at 55 to 58° C., and thereafter it was poured into a mixed liquid of ethyl acetate (100 ml) and ice-water (100 ml) and was then adjusted to have pH of 5 with 1N hydrochloric acid. The organic layer separated was combined with an extract obtained by extracting the aqueous layer with ethyl acetate and then washed with water (3×100 ml) and with saline solution. This was dried over magnesium sulfate, and the solvent was removed by distillation. The residue was triturated with diisopropyl ether, and the precipitates were taken out by filtration and washed with a small amount of diisopropyl ether and then with n-hexane to obtain ethyl 4,5-difluoro-2,3-dihydro-1-methyl-7-oxo-1H, 7H-pyrido[3,2,1-i, j}cinnoline-3,3-bis(tert-butoxycarbonyl)-8-carboxylate as a pale yellow powder.

Example 7

Methylene chloride solution (0.667 ml) of 1M titanium tetrachloride was gradually added to a solution of methylene chloride (2 ml) and tetrahydrofuran (54.3 μ) containing ethyl 6,7,8-trifluoro-1-methylamino-1,4-dihydro-4-oxoquinoline-3-carboxylate (200 mg), with stirring under ice-cooling, and then tert-butyl 2-tert-butoxycarbonylacrylate (0.228 g) was added thereto and stirred for 10 minutes with ice-cooling and then for 15 hours at room temperature. The mixture was poured into a mixture of ethyl acetate (20 ml) and water (20 ml). The organic layer separated was washed with brine and dried over magnesium sulfate, and the solvent was removed by distillation under reduced pressure. The residue was then triturated with n-hexane. The precipitates were taken out by filtration and dried with air to obtain ethyl 6,7,8-trifluoro-1-[N-methyl-N-{2,2-bis(tert-butoxycarbonyl)ethyl}amino]-1,4-dihydro-4-oxoquinoline-3-carboxylate (775.8 mg) as a pale yellow powder.

Example 8

A solution of ethyl 4,5-difluoro-2,3-dihydro-1-methyl-7-oxo-1H, 7H -pyrido[3,2,1-i, j]cinnoline-3,3-bis(tert-butoxycarbonyl)-8-carboxylate (100 mg) in glacial acetic acid (1 ml) was treated with 6M-hydrochlone acid (1 ml) and the solution warmed to reflux for 4 hours. After cooling, ethyl acetate was added and the solution washed with water 4 times, dried over magnesium sulfate, filtered, evaporated under reduced pressure and dried under high vacuum to yield 4,5-difluoro-2,3-dihydro-1-methyl-7-oxo -1H, 7H-pyrido[3,2,1-i,j]cinnoline-3,3-carboxy-8-carboxylic acid (49.5 mg).

NMR(DMSO-d6, δ): 2.89(3H, s), 4.03(2H, d, J=7 Hz), 4.40(1H, t, J=6 Hz), 8.31(1H, dd, J=8.5 Hz), 8.83(1H, s), 13.60–13.00(1H, bs), 14.66(1H, bs)

Example 9

A solution of 4,5-difluoro-2,3-dihydro-1-methyl-7-oxo-1H, 7H-pyrido[3,2,1-i, j]cinnoline-3-carboxy-8-carboxylic acid (42 mg) in dimethyl sulfoxide (2 ml) was placed on a preheated oil bath at 150° C. for 20 minutes, then cooled to room temperature. Ethyl acetate (50 ml) was added and the solution washed with water (4×25 ml), dried over magnesium sulfate, filtered, evaporated under reduced pressure and dried under high vacuum to yield 4,5-difluoro-2,3-dihydro-1-methyl-7-oxo-1H, 7H-pyrido[3,2,1-i, j]cinnoline-8-carboxylic acid (25 mg) as a white solid.

NMR(DMSO-d6, δ): 2.89(3H, s), 3.14(2H, t, J=6Hz), 3.54(2H, t, J=6 Hz), 8.17(1H, dd, J=8.6 and 10.5 Hz), 8.94(1H, s), 14.79(1H, bs)

Example 10

Ethyl 1-methylamino-5,6,7,8-tetrafluoro-1,4-dihydro-4-oxoquinoline-3-carboxylate (9.5 g) and di-tert-butyl methylidenemalonate (13.7 g) were dissolved in methylene chloride (90 ml). Titanium tetrachloride (3.3 ml) was dropwise added thereto with ice-cooling over a period of 40 minutes, and the mixture was then stirred for one hour. The reaction solution was poured into ice-water, the organic layer was separated and dried over magnesium sulfate, and the solvent was removed by distillation. The oily product obtained was subjected to silica gel column chromatography (eluent solvent: ethyl acetate/methylene chloride of 1/20 v/v) to obtain ethyl 1-[N-{2,2-bis(tert-butoxycarbonyl)ethyl}-N-methyl]amino-5,6,7,8-tetrafluoro-1,4-dihydro-4-oxoquinoline-3-carboxylate (8.6 g).

mp: 118°–122° C. NMR(CDCl3, δ): 1.39(12H, s), 1.46(9H, s), 3.00(3H, s), 3.19–3.23(1H, m), 3.48–3.62(2H, m), 4.40(2H, q, J=1 Hz), 8.52(1H, s)

Example 11

Ethyl 1-[N-{2,2-bis(tert-butoxycarbonyl)ethyl}-N-methyl]amino-5,6,7,8-tetrafluoro-1,4-dihydro-4-oxoquinoline-3-carboxylate (10.0 g) was dissolved in dimethylsulfoxide (150 ml) and stirred at room temperature. Cesium carbonate (3.0 g) was added thereto and the mixture was stirred for 3 hours at 80° C. After left to be cooled, the reaction solution was poured into a mixture comprising 5% aqueous citric acid solution (500 ml) and ethyl acetate (500 ml), the organic layer was separated and dried over magnesium sulfate, and the solvent was removed by distillation. The residue was dissolved in ether, and the insoluble substances were removed by filtration. The filtrate was distilled, and the residue was subjected to silica gel chromatography (eluent solvent: chloroform) to obtain ethyl 3,3-bis(tert-butoxycarbonyl)-4,5,6-trifluoro-2,3-dihydro-1-methyl-7-oxo-1H, 7H-pyrido[3,2,1-i,]cinnoline-8-carboxylate (1.6 g).

mp: 169°–173° C. NMR(CDCl3, δ): 1.40(3H, t, J=7.1 Hz), 1.49(18H, s), 2.76(3H, s), 4.04(2H, s), 4.39(2H, q, J=7.1 Hz), 8.47(1H, s)

Example 12

Ethyl 3,3-bis(tert-butoxycarbonyl)-4,5,6-trifluoro-2,3-dihydro-1-methyl-7-oxo-1H, 7H-pyrido[3,2,1-i, j]cinnoline-8-carboxylate (1.0 g) was dissolved in trifluoroacetic acid (2 ml) and heated at 60° C. for 2 hours. The reaction solution was poured into isopropyl ether (50 ml), and the crystals thus precipitated were taken out by filtration to obtain 4,5,6-trifluoro-2,3-dihydro-1-methyl-7-oxo-8-ethoxycarbonyl-1H, 7H-pyrido[3,2,1-i, j]cinnoline-3-carboxylic acid (0.67 g).

mp: 219°–223° C. (dec) NMR(DMSO-d6, δ): 1.28(3H, t, J=7.1 Hz), 2.78(3H, s), 3.73–3.76(2H, m), 4.18–4.25(3H, m), 8.45(1H, s)

Example 13

4,5,6-Trifluoro-2,3-dihydro-1-methyl-7-oxo-8-ethoxycarbonyl-1H, 7H -pyrido[3,2,1-i, j]cinnoline-3-carboxylic acid (300 mg) was dissolved in N-methylpyrrolidone (6 ml) and heated at 160° C. for 3 hours. After the reaction solution was left to be cooled, water was added thereto, and this was extracted three times each with chloroform. The organic layer was dried over magnesium sulfate, and the solvent was removed by distillation. The residue was subjected to silica gel chromatography (eluent solvent: chloroform) to obtain ethyl 4,5,6-trifluoro-2,3-dihydro -1-methyl-7-oxo-1H, 7H-pyrido[3,2,1-i, j]cinnoline-8-carboxylate (128 mg).

mp: 236°–240° C. NMR(CDCl3, δ): 1.40(3H, t, J=7.1 Hz), 2.83(3H, s), 3.00–3.08, 3.44–3.51 (each 2H, each m), 4.38(2H, q, J=7.1 Hz), 8.49(1H, s)

Example 14

Ethyl 4,5,6-trifluoro-2,3-dihydro-1-methyl-7-oxo-1H, 7H-pyrido[3,2,1-i, j]cinnoline-8-carboxylate (30 mg) was added to a mixture of acetic acid (0.4 ml) and 12N hydrochloric acid (0.1 ml) and heated at 100° C. for 2 hours. After the reaction solution was left to be cooled, water was added thereto, and the crystals as precipitated were taken out by filtration. These were washed with water, ethanol and ether to obtain 4,5,6-trifluoro-2,3-dihydro-1-methyl-7-oxo-1H, 7H-pyrido[3,2,1-i, j]cinnoline-8-carboxylic acid (22 mg).

mp: 255°–260° C. (dec.) NMR(DMSO-d6, δ): 2.85(3H, s), 3.10–3.07, 3.55–3.49(each 2H, each m), 8.78(1H, s)

Example 15

Ethyl 4,5,6-trifluoro-2,3-dihydro-1-methyl-7-oxo-1H, 7H-pyrido[3,2,1-i, j]cinnoine-8-carboxylate (62 mg) and benzylamine (50 mg) were added to toluene (2 ml) and heated at 80° C. for 24 hours. The reaction solution was dissolved in chloroform, washed with 5% citric acid aqueous solution and dried over magnesium sulfate, and the solvent was removed by distillation. The crystals obtained were dispersed in ether and taken out by filtration to obtain ethyl 4,5-difluoro-6-benzylamino-2,3-dihydro -1-methyl-7-oxo-1H, 7H-pyrido[3,2,1-i, j]cinnoline-8-carboxylate (59 mg).

mp: 186°–190° C. NMR(CDCl3, δ): 1.38(3H, t, J=7.3 Hz), 2.78(3H, s), 2.90–2.83, 3.33–3.39(each 2H, each m), 4.36(2H, q, J=7.3 Hz), 4.68, 4.70(each 1H, each d, each J=3.9 Hz), 7.22–7.38(5H, m), 8.40(1H, s), 10.81 (1H, brs)

Example 16

Ethyl 4,5-difluoro-6-benzylamino-2, 3-dihydro-1-methyl-7-oxo-1H, 7H-pyrido[3,2,1-i, j]cinnoline-8-carboxylate (59 mg) was dissolved in a mixture of ethanol (10 ml) and acetic acid (10 ml), and 10% palladium-carbon (5 mg) was added thereto and stirred for 24 hours in hydrogen atmosphere. The catalyst was removed by filtration, and the filtrate was subjected to distillation. The residue was dissolved in chloroform, washed with saturated sodium hydrogencarbonate aqueous solution and dried over magnesium sulfate, and then the solvent was removed by distillation. The crystals thus precipitated out were dispersed in ether and taken out by filtration to obtain ethyl 4,5-difluoro-6-amino-2,3-dihydro-1-methyl-7-oxo-1H, 7H-pyrido[3,2,1-i, j]cinnoline-8-carboxylate (27 mg).

mp: 255°–257° C. NMR(CDCl3, $\delta$): 1.39(3H, t, J=7.1 Hz), 2.80(3H, s), 2.89, 3.39(ezch 2H, each t, each J=6.0 Hz), 4.38(2H, q, J=7.1 Hz), 7.03(2H, brs), 8.44(1H, s)

Example 17

Ethyl 4,5-difluoro-6-amino-2,3-dihydro-1-methyl-7-oxo-1H, 7H-pyrido[3,2,1-i, j]cinnoline-8-carboxylate (20 mg) was added to a mixture of acetic acid (0.4 ml) and 12N hydrochloric acid (0.1 ml) and heated at 100° C. for 2 hours. After the reaction solution was left to be cooled, water was added thereto and the crystals as precipitated were taken out by filtration. These were washed with water, ethanol and ether in order to obtain 4,5-difluoro-6-amino-2,3-dihydro-1-methyl-7-oxo-1H,-pyrido [3,2,1-i, j]cinnoline-8-carboxylic acid (13 mg).

mp: >290° C. NMR(DMSO-d6, $\delta$): 2.80(3H, s), 2.86–2.91, 3.40–3.45(each 2H, each m), 7.71(2H, brs), 8.61(1H, s)

Example 18

A suspension of ethyl 1-{N-(allyloxycarbonyl)acetyl-N-methylamino}-6,7,8-trifluoro-1,4-dihydro-4-oxoquinoline-3-carboxylate (1.00 g), cuprous iodide (0.10 g) and potassium tert-butoxide (0.56 g) in dimethyl sulfoxide (5 ml) was stirred at 100°–105° C. for 1.5 hours in nitrogen. Glacial acetic acid (0.16 ml) was added to the reaction mixture. After cooling, acetone (15 ml) was added to the reaction mixture to give a solid. The solid was collected by filtration, washed with water, and dried over phosphorus pentaoxide under reduced pressure to give 3-allyl 8-ethyl 4,5-difluoro-2,3-dihydro-1-methyl-2,7-dioxo-1H, 7H-pyrido[3,2,1-i, j]cinnoline-3,8-dicarboxylate(0.83 g).

Example 19

To a stirred solution of palladium acetate (11 mg) and triphenylphosphine (26 mg) in a mixture of dimethylformamide (2 ml) and tetrahydrofuran (10 ml) was added a mixture of formic acid (0.09 ml) and triethylamine (0.41 ml) in tetrahydrofuran (1 ml)at ambient temperature in nitrogen atmosphere. To the mixture was added 3-allyl 8-ethyl 4,5-difluoro-2,3-dihydro-1-methyl-2,7-dioxo-1H, 7H-pyrido[3,2,1-i, j]cinnoline -3,8-dicarboxylate(0.41 g) and the mixture was stirred at ambient temperature for 4 hours to give a solid. The solid was collected by filtration and dried over phosphorus pentaoxide under reduced pressure to give ethyl 4,5-difluoro-2,3-dihydro-1-methyl-2,7-dioxo-1H, 7H-pyrido[3,2,1-i, j]cinnoline-8-carboxylate(148 mg).

Example 20

A suspension of ethyl 1-{N-(diphenylmethyloxycarbonyl)acetyl-N-methylamino}-6,7,8-trifluoro-1,4-dihydro-4-oxoquinoline-3-carboxylate (3.68 g), cuprous iodide (0.25 g) and potassium tert-butoxide (1.60 g) in dimethyl sulfoxide (18.4 ml) was stirred at 50°–55° C. for 30 minutes in nitrogen atmosphere and at 100°–105° C. for 1.5 hours. Glacial acetic acid (0.5 ml) was added to the mixture . The mixture was poured into water (185 ml) to give a solid. The solid was collected by filtration, washed with acetone, and dried over phosphorus pentaoxide under reduced pressure to give 3-diphenylmethyl 8-ethyl 4,5-difluoro-2,3-dihydro-1-methyl-2,7-dioxo-1H, 7H-pyrido[3,2,1-i, j]cinnoline-3,8-dicarboxylate(1.87 g).

mp: >260° C. IR(Nujol): 1729, 1676 cm$^{-1}$ NMR(DMSO-d6, $\delta$): 1.27(3H, t, J=7.1 Hz), 3.34(3H, s), 4.20(2H, q, J=7.1 Hz), 6.79 (1H, s), 7.1–7.6(11H, m), 8.52(1H, s) MS: 393, 291, 282, 236, 220, 184, 167

Example 21

To a solution of 3-diphenylmethyl 8-ethyl 4, 5-difluoro-2,3-dihydro-1-methyl-2,7-dioxo-1H, 7H-pyrido[3,2,1-i, j]cinnoline-3,8-dicarboxylate(1.51 g) in a mixture of anisole (1.5 ml) and trifluoroacetic acid (30 ml) was stirred at ambient temperature for one hour,. The mixture was concentrated under reduced pressure to give a residue. The residue was subjected to a column chromatography on silica gel (30 g) and eluted with a mixture of methanol and dichloromethane (1:99 and then 2:98 v/v) to give ethyl 4,5-difluoro-2,3-dihydro-1-methyl-2,7-dioxo-1H, 7H-pyrido[3,2,1-i, j]cinnoline-8-carboxylate(0.62 g).

mp: 245° C. (dec.) IR(Nujol): 1727, 1685 cm$^{-1}$ NMR(DMSO-d6, $\delta$): 1.30(3H, t, J=7.1 Hz), 3.68(3H, s), 4.06(2H, s), 4.26(2H, q, J=7.1 Hz), 7.98(1H, dd, J=8.5 Hz, 10.5 Hz), 8.84(1H, s) MS: 322(M+), 277, 250, 220

Example 22

A suspension of ethyl 1-{N-(ethoxycarbonyl)acetyl-N-methylamino}-6,7,8-trifluoro-1,4-dihydro-4-oxoquinoline-3-carboxylate (1.00 g), cuprous iodide (0.10 g), and potassium tert-butoside (0.57 g) in dimethyl sulfoxide (5 ml) was stirred at 100°–105° C. for 1.5 hours in nitrogen atmosphere. After cooling, acetone (15 ml) was added to the reaction mixture to give a solid. The solid was collected by filtration, washed with water, and dried over phosphorus pentaoxide under reduced pressure to give diethyl 4,5-difluoro-2,3-dihydro-1-methyl-2,7-dioxo-1H, 7H-pyrido [3,2,1-i, j]cinnoline-3,8-dicarboxylate (0.87 g).

mp: >260° C. IR(Nujol): 1675 cm$^{-1}$ NMR(CDCl3, $\delta$): 7.14(1H, dd, J=7.7 Hz, 10.5 Hz), 8.48(1H, s) MS: 394(M+), 349(M+ −45), 345, 322, 307

Example 23

A suspension of ethyl 1-{N-(ethoxycarbonyl)acetyl-N-methylamino}-6,7,8-trifluoro-1,4-dihydro-4-oxoquinoline-3-carboxylate (0.10 g) and potassium fluoride (0.056 g) in dimethylformamide (0.5 ml) was stirred at 100°–105° C. for 5 hours in nitrogen atmosphere. After cooling, water (5 ml) was added to the reaction mixture to give a solid. The solid was collected by filtration, washed with acetone, and dried over phosphorus pentaoxide under reduced pressure to give diethyl 4,5-difluoro-2,3-dihydro-1-methyl-2,7-dioxo-1H, -pyrido[3,2,1-i, j]cinnoline-3,8-dicarboxylate(52 mg).

Example 24

A suspension of ethyl 1-{N-(ethoxycarbonyl)acetyl-N-methylamino}-6,7,8-trifluoro-1,4-dihydro-4-oxoquinoline-3-carboxylate (0.20 g), cuprous iodide (0.02 g), and sodium hydride (60% in oil suspension, 0.04 g) in dimethylformamide (1 ml)was stirred at 100°–105° C. for 4 hours in nitrogen atmosphere. After cooling, water (10 ml) was added to the mixture to give a solid. The solid was collected by filtration, washed with water, and dried over phosphorus pentaoxide under reduced pressure to give diethyl 4,5-difluoro-2,3-dihydro-1-methyl-2,7-dioxo-1H, 7H-pyrido [3,2,1-i, j]cinnoline-3,8-dicarboxylate(0.16 g).

Example 25

A solution of diethyl 4,5-difluoro-2,3-dihydro-1-methyl-2,7-dioxo -1H, 7H-pyrido[3,2,1-i, j]cinnoline-3,8-dicarboxylate(100 mg) in a mixture of water (0.05 ml) and trifluoroacetic acid (1.0 ml) was heated under reflux for 3 hours. The mixture was purified by preparative thin layer chromatography (development with ethyl acetate) to give ethyl 4,5-difluoro-2,3-dihydro-1-methyl-2,7-dioxo-1H, 7H-pyrido[3,21i, j]cinnoline -8-carboxylate(36 mg).

Example 26

To a suspension of ethyl 4,5-difluoro-2,3-dihydro-1-methyl-2,7-dioxo-1H, 7H-pyrido[3,2,1-i, j]cinnoline-8-carboxylate(200 mg) in tetrahydrofuran (2 ml) was added borane-methyl sulfide complex (0.1 ml) under ice-cooling and the mixture was stirred at ambient temperature for 6 days. Methanol (0.5 ml) was added to the reaction mixture under ice-cooling and the mixture was stirred at ambient temperature for one hour. The mixture was concentrated under reduced pressure and purified by preparative thin layer chromatography (development with ethyl acetate) to give ethyl 4,5-difluoro-2,3-dihydro-1-methyl-7-oxo-1H, 7H-pyrido[3,2,1-i, j]cinnoline-8-carboxylate(5.3 mg).

Example 27

To a suspension of diethyl 4,5-difluoro-2,3-dihydro-1-methyl-2,7-dioxo-1H, 7H-pyrido[3,2,1-i, j]cinnoline-3,8-dicarboxylate(510 mg) in a mixture of concentrated hydrochloric acid (0.61 ml) and glacial acetic acid (3.06 ml) was heated at 100°–105° C. for 5 hours. After cooling, water (15.3 ml) was added to the mixture. The resulted solid was collected by filtration and dried over phosphorus pentaoxide under reduced pressure to give 4,5-difluoro-2,3-dihydro-1-methyl-2,7-dioxo-1H, 7H-pyrido[3,2,1-i, j]cinnoline-8-carboxylic acid (287 mg).

Example 28

Pyridine (2 ml) suspension containing ethyl 4,5-difluoro-2,3-dihydro-1-methyl-2,7-dioxo-1H, 7H-pyrido[3,2,1-i, j]cinnoline-8-carboxylate (300 mg) and sodium boron hydride (100 mg) was refluxed for 8 hours in nitrogen atmosphere. The solid was separated by filtration, and the filtrate was concentrated under reduced pressure to obtain a syrup product. The syrup product was purified by a previously prepared thin layer chromatography (using ethyl acetate as a developer), to obtain ethyl 4,5-difluoro-2,3,7,8-tetrahydro-1-methyl-7-oxo-1H, 7H-pyrido[3,2,1-i. j]cinnoline-8-carboxylate (36.7 mg) having Rf value of 0.82 and ethyl 4,5-difluoro-2,3-dihydro-1-methyl-7-oxo-1H, 7H-pyrido[3,2,1-i, j]cinnoline -8-carboxylate (5.6 mg) having Rf value of 0.48.

Physical properties of ethyl 4,5-difluoro-2,3,7,8-tetrahydro-1-methyl-7-oxo-1H, 7H-pyrido[3,2,1-i. j]cinnoline-8-carboxylate were as follows:

mp: 82°–84° C. IR(Nujol): 1658, 1630 cm$^{-1}$ MS: 310, 295, 237

Example 29

Sodium boron hydride (46 mg) was added to a mixture solution of boron trifluoride-diethyl ether complex (0.15 ml) and tetrahydrofuran containing ethyl 4,5-difluoro-2,3-dihydro-1-methyl-2,7-dioxo-1H, 7H-pyrido [3,2,1-i., j]cinnoline-8-carboxylate (100 mg), with ice-cooling, and the mixture was stirred for one hour at room temperature. The solid was removed by filtration, and the filtrate was concentrated under reduced pressure to obtain a syrup product. The syrup product was purified by a previously prepared thin layer chromatography (using ethyl acetate as a developer), to obtain ethyl 4,5-difluoro-2,3-dihydro-1-methyl-7-oxo-1H, 7H-pyrido[3,2,1-i. j]cinnoline-8-carboxylate (7.9 mg) and ethyl 4,5-difluoro-2,3,7,8-tetrahydro-1-methyl-7-oxo-1H, -pyrido[3,2,1-i, j]cinnoline-8-carboxylate (3.5 mg).

Example 30

Active manganese dioxide (30 mg) was added to ethyl acetate (1 ml) solution of ethyl 4,5-difluoro-2,3,7,8-tetrahydro-1-methyl-7-oxo-1H, 7H-pyrido[3,2,1-i, j]cinnoline-8-carboxylate (20 mg), and the mixture was stirred for 2 days at room temperature. The solid was removed by filtration, and the filtrate was concentrated under reduced pressure to obtain a syrup product. The syrup product was purified by a previously prepared thin layer chromatography (using ethyl acetate as a developer), to obtain ethyl 4,5-difluoro-1-methyl-7-oxo-1H, 7H-pyrido[3,2,1-i, j]cinnoline-8-carboxylate (11.2 mg).

Example 31

To dioxane (1 ml) suspension of sodium boron hydride (60 ml), was added dioxane (0.2 ml) solution of trifluoroacetic acid (181 mg) at 10° C. or lower. To the mixture, was added ethyl 4,5-difluoro-2,3-dihydro-1-methyl-2,7-dioxo-1H, 7H-pyrido[3,2,1-i, j]cinnoline-8-carboxylate (100 mg). The mixture was heated at 100° to 105° C. for 5 hours. After cooled, the solid was removed by filtration, and the filtrate was concentrated under reduced pressure to obtain a syrup product. The syrup product was purified by a previously prepared thin layer chromatography (using ethyl acetate as a developer), to obtain ethyl 4,5-difluoro-2,3-dihydro-1-methyl-7-oxo-1H, 7H-pyrido[3,2,1-i, j]cinnoline-8-carboxylate (9.4 mg).

Example 32

Ethyl 4,5-difluoro-2,3-dihydro-1-methyl-2,7-dioxo-1H, 7H-pyrido[3,2,1-i, j]cinnoline-8-carboxylate (100 mg) was added to phosphoryl chloride (0.35 ml) at room temperature. The mixture was stirred for 1.5 hours, and the excess phosphoryl chloride was removed at 20° C. (20 mmHg). The oily product thus formed was left under high vacuum for 30 minutes to remove the remaining phosphoryl chloride, and the residue was dissolved in ethylene glycol dimethyl ether (5 ml). The solution was cooled in an ice bath, and sodium boron hydride was added thereto with vigorously stirring. The mixture was stirred for one hour at room temperature, and 1N hydrochloric acid (1 ml) was dropwise added thereto. The solvent was removed by distillation, and water (3 ml) was added to the residue. The precipitates formed were taken out by filtration and dissolved in ethyl acetate, and the solution was purified by a previously prepared thin layer chromatography (using ethyl acetate as a developer) to obtain ethyl 4,5-difluoro-2,3-dihydro-1-methyl-7-oxo-1H, 7H-pyrido[3,2,1-i, j]cinnoline-8-carboxylic acid (10.0 mg).

Example 33

A solution of ethyl 4,5-difluoro-2,3-dihydro-1-methyl-2,7-dioxo-1H, 7H-pyrido[3,2,1-i, j]cinnoline-8-carboxylate(152 mg) in a mixture of concentrated hydrochloric acid (0.2 ml) and glacial acetic acid (1 ml) was refluxed for 5 hours. After cooling, water (5 ml) was added to the mixture. A obtained solid was collected by filtration and dried over phosphorus pentaoxide under reduced pressure to give 4,5-difluoro-2,3-dihydro-1-methyl-2,7-dioxo-1H, 7H-pyrido[3,2,1-i, j]cinnoline-8-carboxylic acid(111 mg).

mp: >260° C. IR(Nujol): 1735, 1675 cm$^{-1}$ NMR(DMSO-d$_6$, δ): 3.77(3H, s), 4.16(2H, s), 8.23(1H, dd, J=8.3 Hz, 10.1 Hz, 10.1 Hz), 9.06 (1H, s) MS: 294(M+), 250, 221

Example 34

Dimethylformamide (7.5 ml) solution of diethyl malonate (239 μl) was added to sodium hydride (122 mg) with stirring under ice-cooling and was stirred for 20 minutes with ice-cooling. To the solution was added ethyl 1-[N-(chloromethyl)-N-methylamino]-6,7,8-trifluoro-1,4-dihydro-4-oxoquinoline-3-carboxylate (500 mg), and the mixture was stirred for one hour with ice-cooling. This was then heated up to 50° C. and stirred for 3 hours to effect ring-closing reaction. The reaction solution was added to a mixture solution comprising ethyl acetate (150 ml) and water (150 ml) for extraction. The organic layer was washed with water (150 ml×3) and with saturated brine(100 ml×1), dried over magnesium sulfate and then concentrated under reduced pressure. The residue thus obtained was subjected to silica gel (15 g) column chromatography, eluted with a mixed solvent comprising dichloromethane and ethyl acetate (20/1 to 10/1) and concentrated to dryness under reduced pressure to obtain ethyl 4,5-difluoro-2,3,-dihydro-1-methyl-7-oxo-1H, 7H-pyrido[3,2,1-i, j]cinnoline-3,3-bis(ethoxycarbonyl)-8-carboxylate (183 mg).

IR(Nujol): 1730, 1610, 1560 cm$^{-1}$ NMR (CDCl$_3$, δ): 1.30(6H, t, J=7 Hz), 1.40(3H, t, J=7 Hz), 2.77(3H, s), 4.14(2H, s), 4.20–4.45(6H, m), 8.28–8.37(1H, m), 8.55(1H, s)

Example 35

In a similar manner as in Example 34, the following compound was obtained.

Ethyl 4,5-difluoro-2,3-dihydro-1-methyl-7-oxo-1H, 7H, -pyrido[3,2,1-i, j]cinnoline-3,3-bis(tert-butoxycarbonyl)-8-carboxylate NMR (CDCl$_3$, δ): 1.37(3H , t, J=7 Hz), 1.48(18 H, s), 2.78(3H, s), 4.07(2H, s), 4.39(2H, q, J=7 Hz), 8.25–8.34(1H, m), 8.54(1H, s)

Referential Example 1

4,5-difluoro-6-amino-2,3-dihydro-1-methyl-7-oxo-1H, 7H-pyrido[3,2,1-i, j]cinnoline-8-carboxylic acid (4 mg) and pyrrolidine (10 μl) were added to acetonitrile (1 ml) and heated at 80° C. for 3 hours, and the solvent was removed by distillation. The residue was washed with ethanol and ether in order to obtain 5-fluoro-4-(pyrrolidin-1-yl)-6-amino-2,3-dihydro-1-methyl-7-oxo-1H, 7H-pyrido[3,2,1-i, j]cinnoline-8-carboxylic acid (2 mg).

mp: >290° C. NMR(CDCl3, δ): 1.97–2.06(4H, m), 2.79–2.85(2H, m), 2.86(3H, s), 3.30–3.35 (2H, m), 3.44–3.53(4H, m), 6.57(2H, brs), 8.66(1H, s)

We claim:

1. A compound of the formula:

[Chemical structure diagram showing a tricyclic compound with substituents X$^1$, X$^2$, X$_a^5$, COOR$^1$, A, B, N, N-R$^2$]

wherein

R$^1$ is a hydrogen atom or a carboxyl-protecting group;

R$^2$ is a hydrogen atom or a lower alkyl group;

X$^1$ is a hydrogen atom or a halogen atom;

X$^2$ is a halogen atom;

X$_a^5$ is a hydrogen atom or a halogen atom;

A is a methylene group; a group of >CH—COOR$^4$, or a group of:

[Chemical structure: >C< with COOR$^5$ and COOR$^6$]

in which R$^4$, R$^5$ and R$^6$ each are a hydrogen atom or a carboxyl-protecting group;

B is a methylene group or a carbonyl group; provided that both A and B must not be methylene groups at the same time, or a pharmaceutically acceptable salt thereof.

2. A compound of claim 1, wherein R$^1$, R$^4$, R$^5$ and R$^6$ each are a carboxyl-protecting group.

3. A compound of claim 2, wherein

A is a methylene group; and
B is a carbonyl group,
A is a group of >CH—COOR$^4$;
wherein R$^4$ is a hydrogen atom or a carboxyl-protecting group, and B is a methylene group or a carbonyl group, or
A is a group of:

[Chemical structure: >C< with COOR$^5$ and COOR$^6$]

wherein

R$^5$ and R$^6$ are each as defined above; and
B is a methylene group.

4. A compound of claim 2, wherein

R$^1$ is a hydrogen atom or a lower alkyl group;
R$^2$ is a lower alkyl group;
X$^1$ is a halogen atom;
R$^4$, R$^5$ and R$^6$ each are a hydrogen atom or a lower alkyl group.

* * * * *